(12) United States Patent
Yamamoto

(10) Patent No.: US 8,947,079 B2
(45) Date of Patent: Feb. 3, 2015

(54) EDDY CURRENT MEASURING SENSOR AND INSPECTION METHOD USING THIS EDDY CURRENT MEASURING SENSOR

(75) Inventor: Takanari Yamamoto, Toyota (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 349 days.

(21) Appl. No.: 13/521,153

(22) PCT Filed: Dec. 21, 2010

(86) PCT No.: PCT/IB2010/003312
§ 371 (c)(1),
(2), (4) Date: Aug. 8, 2012

(87) PCT Pub. No.: WO2011/086414
PCT Pub. Date: Jul. 21, 2011

(65) Prior Publication Data
US 2013/0009632 A1 Jan. 10, 2013

(30) Foreign Application Priority Data
Jan. 14, 2010 (JP) .................................. 2010-006289

(51) Int. Cl.
*G01N 27/82* (2006.01)
*G01N 27/90* (2006.01)

(52) U.S. Cl.
CPC .................................. *G01N 27/9046* (2013.01)
USPC ........................................................ 324/240

(58) Field of Classification Search
CPC ........................................................ G01R 33/12
See application file for complete search history.

(56) References Cited

U.S. PATENT DOCUMENTS

| 3,976,936 A * | 8/1976 | Nishino ......................... 324/232 |
| 5,021,738 A | 6/1991 | Vernon et al. |
| 5,537,037 A | 7/1996 | Otaka et al. |
| 2008/0191693 A1 * | 8/2008 | Jones et al. .................... 324/238 |

FOREIGN PATENT DOCUMENTS

| CN | 101231267 A | 7/2008 |
| EP | 0 177 626 A1 | 4/1986 |

(Continued)

OTHER PUBLICATIONS

Yamamoto, T. et al., Development of Hardening Depth Evaluation Technique using Eddy Current-Establishment and Introduction of In-line Hardening Depth Inspection System, *SAE Paper*, 2009.

(Continued)

*Primary Examiner* — Arleen M Vazquez
*Assistant Examiner* — Feba Pothen
(74) *Attorney, Agent, or Firm* — Oliff PLC

(57) ABSTRACT

An eddy current measuring probe sensor has an exciting portion and a detecting portion. The exciting portion includes a primary exciting portion that includes a main core formed of a cylindrical magnetic body and a main coil that is a solenoid coil wound in a circumferential direction around the main core, and a plurality of secondary exciting portions that include sub-cores formed of cylindrical magnetic bodies that are arranged around the primary exciting portion in a manner such that an axial direction of each of the sub-cores is the same as an axial direction of the main core. The plurality of secondary exciting portions are configured to be able to change the position of each sub-core independently in the axial direction relative to the primary exciting portion.

10 Claims, 21 Drawing Sheets

(56) References Cited

FOREIGN PATENT DOCUMENTS

| EP | 0 332 048 A2 | 9/1989 |
| JP | A-2008-170233 | 7/2008 |
| JP | A-2009-31224 | 2/2009 |
| JP | A-2009-47664 | 3/2009 |
| JP | A-2010-197174 | 9/2010 |

OTHER PUBLICATIONS

International Search Report issued in International Application No. PCT/IB2010/003312 on May 16, 2011.

Written Opinion of the International Searching Authority issued in International Application No. PCT/IB2010/003312 on May 16, 2011.

* cited by examiner

F I G . 9
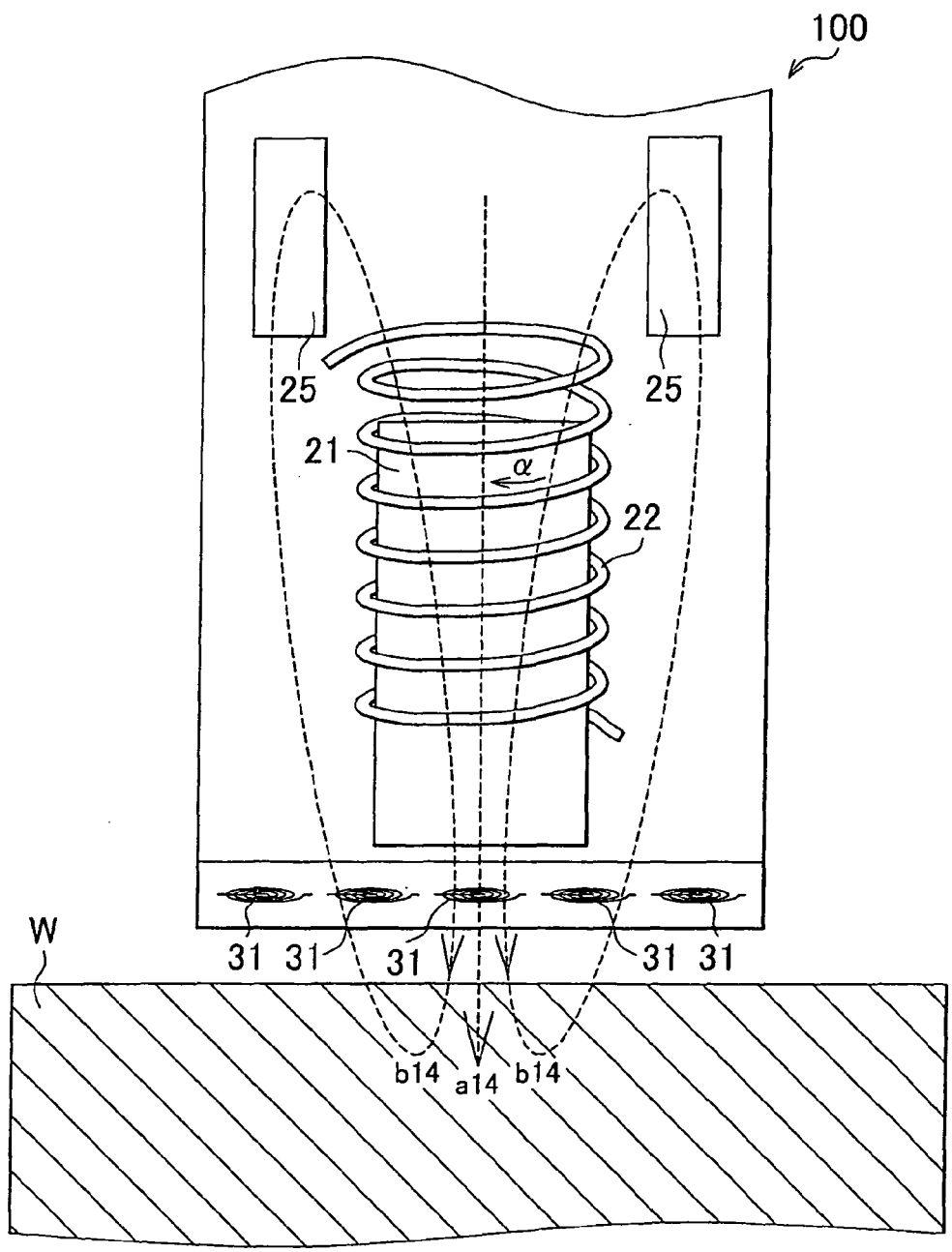

MAGNETISM PERMEATION IMAGE

MAGNETISM PERMEATION IMAGE

EDDY CURRENT MEASURING SENSOR AND INSPECTION METHOD USING THIS EDDY CURRENT MEASURING SENSOR

BACKGROUND OF THE INVENTION

1. Field of the Invention

The invention relates to an eddy current measuring sensor and an inspection method using this eddy current measuring sensor. More particularly, the invention relates to an eddy current measuring sensor that improves the inspection accuracy in eddy current inspection, and an inspection method using this eddy current measuring sensor.

2. Description of the Related Art

Steel that has been induction hardened (hereinafter simply referred to as "steel"), in which metal (conductive material) is hardened by high-frequency induction heating, is used for mechanical parts such as underbody parts and engine parts of tomobiles and motorcycles. With regards to the hardened layer depth of surface hardening (hereinafter also referred to as the "hardening depth") and the hardness in the induction hardening of steel, the effective hardened layer depth and the total hardened layer depth are standardized. Therefore, it is necessary to measure and evaluate the hardening depth and the hardness to ensure the quality of the steel.

The hardening depth and the hardness of the steel is evaluated by cutting out a portion of the steel as a sample, and measuring the sectional strength with any one of a variety of hardness gauges such as a Vickers hardness tester. However, with this destructive inspection method, the steel used as the sample is discarded, which leads to an increase in material costs. Also, in addition to the inspections taking longer, 100% inspection in a line is difficult, so steel may end up being moved to the next process without defects that occur sporadically being detected.

Japanese Patent Application Publication No. 2009-31224 (JP-A-2009-31224) and Japanese Patent Application Publication No. 2009-47664 (JP-A-2009-47664) describe technology for measuring the hardening depth and hardness of steel using an eddy current type inspection that is a nondestructive inspection. In this eddy current type inspection, an alternating current magnetic field is generated by moving an exciting coil carrying alternating current close to the steel. This alternating current magnetic field produces an eddy current in the steel. A detection coil then detects an induction field induced by this eddy current. That is, this eddy current type inspection makes it possible to quantitatively measure the hardening depth and the hardness of steel with 100% inspection and in a short period of time, without discarding the any steel. This eddy current type inspection is also used for flaw detection testing to detect flaws such as cracks in the surface of the object being inspected, and foreign material discrimination testing to detect foreign material in the object being inspected, in addition to hardening depth/hardness measurement testing to measure the hardening depth and the hardness of steel described above.

With regards to the conductivity of steel, there is a difference between the base material and martensite that occurs in the hardened layer. Therefore, in the hardening depth/hardness measurement testing described above, if the steel is measured using an eddy current sensor, the voltage (i.e., the amplitude) detected by the detection coil changes as the hardening depth changes and the voltage detected by the detection coil decreases monotonically as the hardened layer depth increases, so the hardening depth of the steel can be measured using these phenomena.

For example, the technology described in JP-A-2009-31224 is configured to inspect the hardening depth of a shaft portion of a shaft component using an encircling coil (i.e., an annular coil). The encircling coil has a stronger magnetic field than a probe coil does, and the distance to the steel does not need to be precisely controlled, which makes it suitable for hardening depth/hardness measuring testing. However, the diameter of the inner circumference which is the measuring portion of the encircling coil is fixed, so the filling rate of the measured portion with respect to the encircling coil (i.e., the ratio of the cross-section area of the measured portion of the steel to the inner peripheral cross-section area of the encircling coil) changes depending on the outer diameter of the measured portion of the steel. The inspection accuracy of the eddy current type inspection decreases exponentially as the filling rate decreases. Therefore, with the related art, the inspection accuracy differs due to the outer diameter of the steel changing at each measured portion. Also, the steel that is the object being inspected needs to be inserted through the encircling coil, so the range of application of this technology is limited to shaft components with a substantially constant outer diameter. That is, the inspection is difficult to carry out on a component in which the outer diameter changes significantly, such as a crankshaft, for example.

The technology described in JP-A-2009-47664 described above is configured to measure the hardening depth of steel using a probe coil. With the hardening depth/hardness measurement testing, the ratio of detected signal components to noise components is lower than it is with either flaw detection testing or foreign material discrimination testing, so greater inspection accuracy can be obtained. However, the probe coil has a weaker magnetic field and the distance to the steel must be precisely controlled, so while it is suitable for flaw detection testing and foreign material discrimination testing, it is difficult to use for hardening depth/hardness measurement testing.

Further, with the probe coil according to the related art, the magnetic field in the work is unable to be widened or offset to one side, so it is difficult to appropriately control the spread and direction and the like of the magnetic field. Furthermore, in flaw detection testing with the probe coil as well, a so-called edge effect in which a flaw signal ends up getting buried in an edge signal at an end portion of the steel severely limits the inspectable range and the parts that can be inspected and the like, so the reduction of this edge effect in eddy current measurements using a probe coil has become an issue.

SUMMARY OF INVENTION

The invention provides an eddy current measuring sensor that is capable of carrying out a hardening depth/hardness measurement test with high detection accuracy by a strong magnetic field of a probe coil even when inspecting an induction-hardened component having an outer diameter that changes significantly, and that reduces an edge effect by appropriately controlling the spread and direction and the like of the magnetic field, as well as an inspection method using this eddy current measuring sensor.

A first aspect of the invention relates to an eddy current measuring probe sensor provided with an exciting portion and a detecting portion. The exciting portion i) includes a primary exciting portion that includes a main core formed of a cylindrical magnetic body and a main coil that is a solenoid coil wound in a circumferential direction around the main core, and a plurality of secondary exciting portions that include sub-cores formed of cylindrical magnetic bodies that are arranged around the primary exciting portion in a manner such that an axial direction of each sub-core is the same as an axial direction of the main core, the plurality of secondary exciting portions being configured to change the position of each sub-core independently in the axial direction of the main core relative to the primary exciting portion, and ii) applies a predetermined alternating current excitation signal to a component to be measured. The detecting portion detects a detection signal according to an eddy current from the component to be measured to which the predetermined alternating current excitation signal has been applied.

In the sensor of the first aspect, each of the secondary exciting portions may include a sub-coil that is a solenoid coil that is wound in a circumferential direction around the sub-core, and each of the secondary exciting portions may be configured such that a direction of magnetic flux that is generated at the main coil of the primary exciting portion and penetrates the main core is opposite a direction of magnetic flux that is generated in the sub-coil of each of the secondary exciting portions and penetrates the sub core.

In the sensor structured as described above, the primary exciting portion may be configured to change the relative positions of the main coil and the main core independently in the axial direction of the main core.

In the sensor structured as described above, the detecting portion may include a plurality of detection coils radially arranged centered around an axial portion of the primary exciting portion, and the plurality of detection coils may each be independently and selectively made so as to be acknowledged or ignored with regards to detecting the detection signal.

In the sensor structured as described above, the detecting portion may include a plurality of pancake coils or a plurality of planar coils, that are arranged over an entire tip end surface of the exciting portion, and the tip end surface may be a surface on the side of the component to be measured.

In the sensor structured as described above, the detecting portion may include a plurality of vertical solenoid coils arranged in positions in a tip end surface of the exciting portion that are opposite the primary exciting portion and the secondary exciting portion, in a manner such that an axial direction of each of the plurality of vertical solenoid coils is the same as the axial direction of the main core, and a plurality of horizontal solenoid coils radially arranged in positions in the tip end surface of the exciting portion that are between the primary exciting portion and the secondary exciting portion, in a manner such that the axial direction of each of the plurality of horizontal solenoid coils is perpendicular to the axis of the main core.

In the sensor structured as described above, the detecting portion may include a plurality of detection coils that are arranged adjacent to the secondary exciting portions and to the outside of the secondary exciting portions in a radial direction of the main core.

In the sensor structured as described above, the predetermined alternating current excitation signal may be a magnetic field that is generated by applying a predetermined alternating current voltage to the main coil, and the detection signal may be voltage induced by the eddy current.

A second aspect of the invention relates to an inspection method that includes inspecting a component to be measured by performing an eddy current measurement using an eddy current measuring probe sensor provided with an exciting portion that i) includes a primary exciting portion that includes a main core formed of a cylindrical magnetic body and a main coil that is a solenoid coil wound in a circumferential direction around the main core, and a plurality of secondary exciting portions that include sub-cores formed of cylindrical magnetic bodies that are arranged around the primary exciting portion in a manner such that an axial direction of each sub-core is the same as an axial direction of the main core, the plurality of secondary exciting portions being configured to change the position of each sub-core independently in the axial direction of the main core relative to the primary exciting portion, and ii) applies a predetermined alternating current excitation signal to a component to be measured; and a detecting portion that detects a voltage induced by an eddy current that is generated in the component to be measured to which the magnetic field has been applied.

The invention makes it possible to carry out a hardening depth/hardness measurement test with high detection accuracy by a strong magnetic field of a probe coil even when inspecting an induction-hardened component having an outer diameter that changes significantly, and reduce an edge effect by appropriately controlling the spread and direction and the like of the magnetic field.

BRIEF DESCRIPTION OF DRAWINGS

The foregoing and further objects, features and advantages of the invention will become apparent from the following description of embodiments with reference to the accompanying drawings, wherein like numerals are used to represent like elements and wherein:

FIG. 9 is a schematic diagram of a fourth example of the eddy current measuring sensor according to the first embodiment;

DETAILED DESCRIPTION OF EMBODIMENTS

In the embodiments of the invention, an eddy current measuring sensor is formed by a plurality of exciting coils that are exciting portions and a plurality of detection coils that are detecting portions. These embodiments attempt to expand the application range of eddy current measuring by changing the arrangement and connecting method of these coils. Hereinafter, embodiments of the invention will be described. Incidentally, in the embodiments of the invention, a case in which eddy current measuring by an eddy current measuring sensor is used to inspect the hardening quality (i.e., hardening depth and hardening hardness) of a component hardened by induction hardening or the like, i.e., a case in which the hardening quality of a hardened component that is the object to be measured is inspected by performing an eddy current measurement using an eddy current measuring sensor, will be described as the main example.

Figure 1:
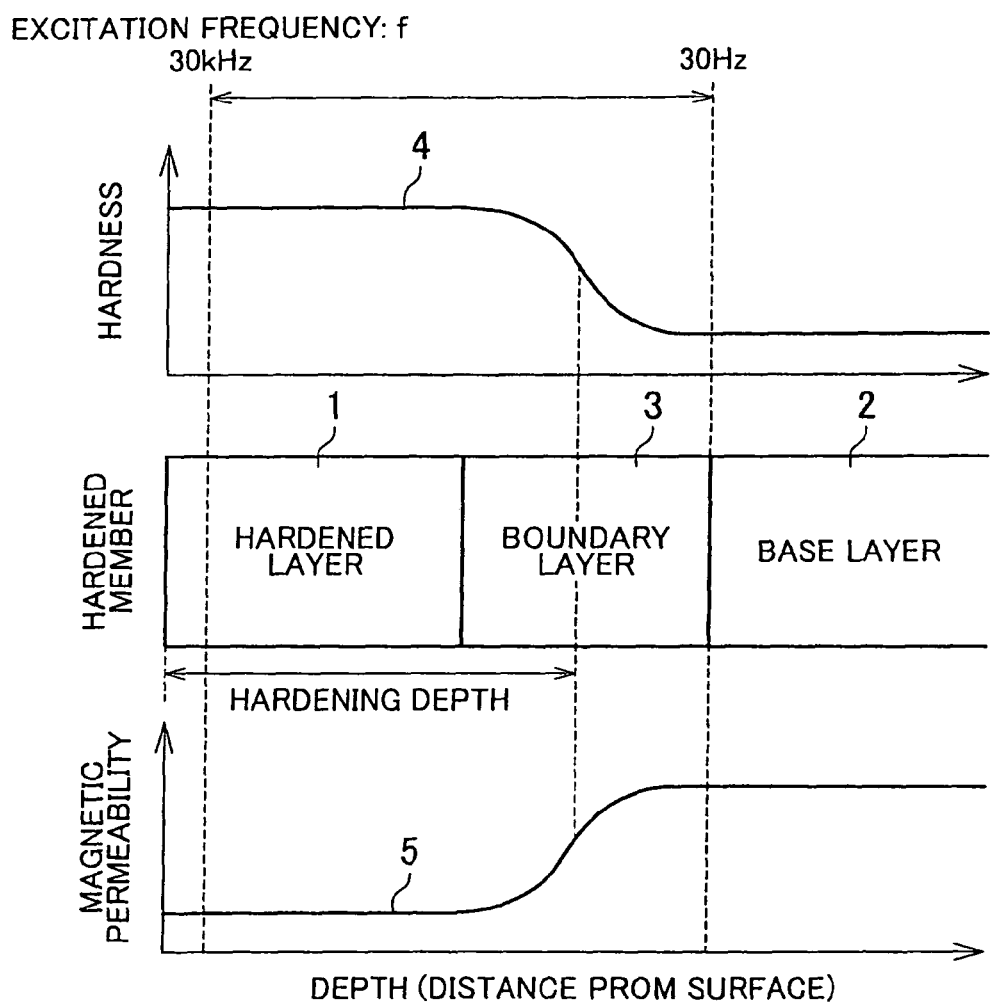
FIG. 1 is a graph showing the relationships among the layer state in the depth direction, the hardness, and the magnetic permeability of a hardened member.

FIG. 1 is a graph showing the relationships among the layer state in the depth direction (i.e., the distance from the surface), the hardness, and the magnetic permeability of a hardened member which is steel (such as S45C) that has been hardened. The general organizational structure of the hardened member is such that a hardened layer 1 which is a portion on the surface side that has been hardened is formed separated from a base layer 2 which is a portion of base material by a boundary layer 3, as shown in FIG. 1. Referring to a hardness change curve 4, the hardened layer 1 and the base layer 2 have different hardnesses, with the hardness of the hardened layer 1 being greater than the hardness of the base layer 2. In the boundary layer 3, the hardness gradually decreases from the hardened layer 1 to the base layer 2. Specific examples of the hardnesses are, when expressed in terms of Vickers hardness (Hv), an Hv of 600 to 700 at the hardened layer 1 and an Hv of approximately 300 at the base layer 2.

Meanwhile, referring to a magnetic permeability change curve 5, the change in magnetic permeability with respect to the distance from the surface of the hardened member is substantially inversely proportionate to the change in hardness with respect to the distance from the surface of the hardness member. That is, with the magnetic permeability, the magnetic permeability of the hardened layer 1 is less than the magnetic permeability of the base layer 2, and in the boundary layer 3, the magnetic permeability gradually increases from the hardened layer 1 side to the base layer 2 side. The eddy current measurement according to this embodiment uses this kind of relationship between the hardness and magnetic permeability with respect to the distance from the surface of the hardened member.

Figure 2:
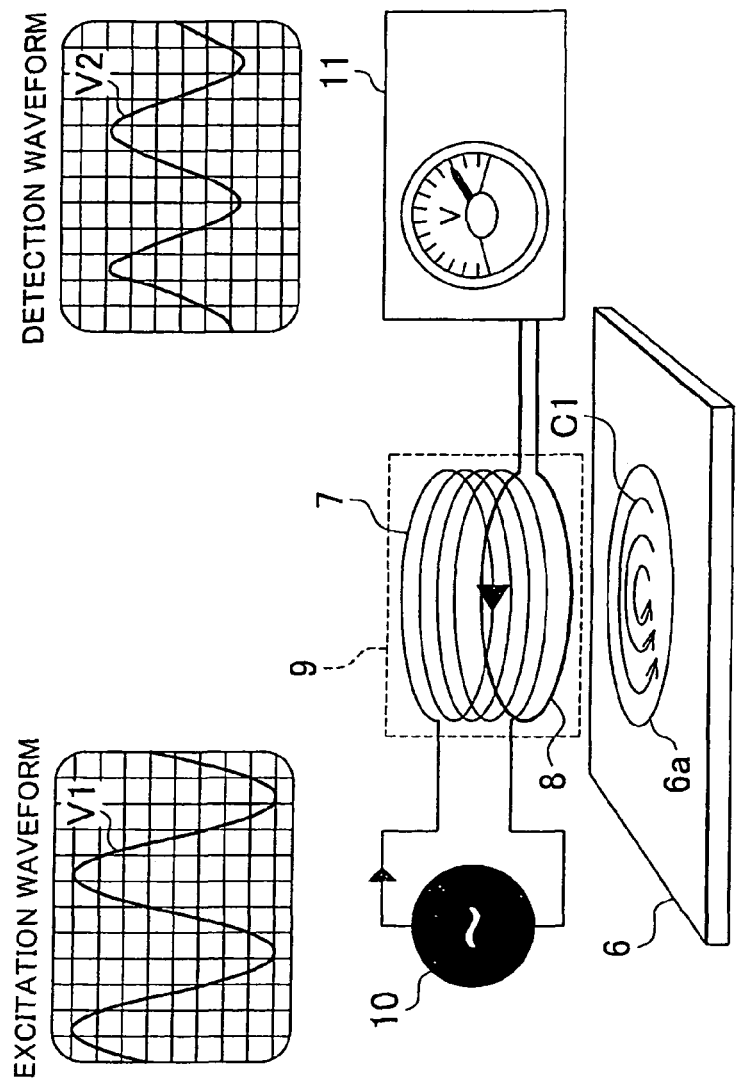
FIG. 2 is a view showing a frame format of the structure of an apparatus for performing an eddy current measurement according to an embodiment of the invention.

An outline (i.e., the measurement principle) of the structure of an apparatus for performing an eddy current measurement according to an embodiment of the invention will be described with reference to FIG. 2. As shown in FIG. 2, in the eddy current measurement, an eddy current measuring sensor 9 that has an exciting coil 7 that is an exciting portion and a detection coil 8 that is a detecting portion is set in a predetermined position with respect to a measured portion 6a of a work (i.e., a magnetic body) 6 that is the component to be measured. In this kind of structure, a magnetic field is generated around the exciting coil 7 when current is supplied to the exciting coil 7. As a result, an eddy current is produced near the surface of the measured portion 6a of the work 6 that is a magnetic body by electromagnetic induction (see arrow C1 in FIG. 2). As the eddy current is produced at the surface of the measured portion 6a, magnetic flux penetrates the detection coil 8, and as a result, inducted voltage is generated in the detection coil 8. This induced voltage is measured by the detection coil 8.

Both ends (i.e., both terminals) of the exciting coil 7 are connected to an alternating current (AC) power supply 10. This AC power supply 10 applies a predetermined alternating current (AC) excitation signal (i.e., an alternating current voltage signal for induction) V1 to the exciting coil 7. Both ends (i.e., both terminals) of the detection coil 8 are connected to a measuring device 11. The measuring device 11 detects the magnitude of a detection signal (i.e., a voltage signal indicative of the induced voltage) obtained from the detection coil 8 when the AC excitation signal V1 is applied from the AC power supply 10 to the exciting coil 7, and a phase difference (i.e., a phase lag) Φ (see FIG. 3) of a detection signal V2 with respect to the AC excitation signal V1. Here, the AC excitation signal V1 (a waveform) is applied to the measuring device 11 as an amplified phase detection in order to detect the phase difference Φ.

Figure 3:
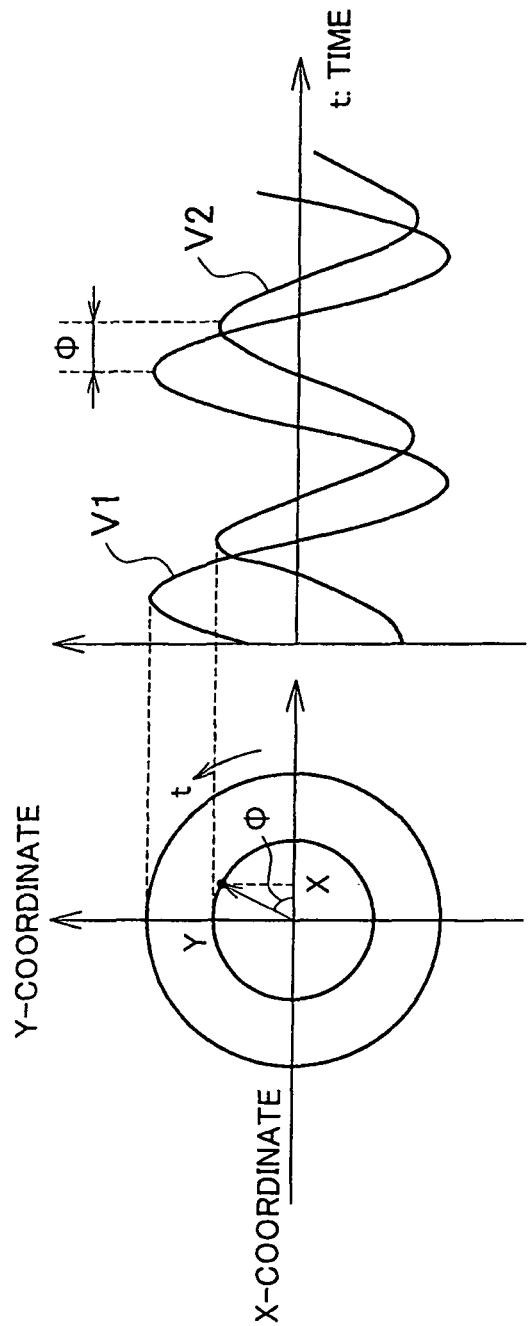
FIG. 3 is a graph showing the relationship between an alternating current excitation signal and a detection signal in the eddy current measurement.

The detection signal V2 detected by the detection coil 8 reflects the magnetic permeability of the measured portion 6a (i.e., the work 6). That is, when the magnetic permeability of the measured portion 6a increases, the magnetic flux that accompanies the generation of the eddy current described above increases, and thus the detection signal V2 increases. Conversely, when the magnetic permeability of the measured portion 6a decreases, the magnetic flux that accompanies the generation of the eddy current described above decreases, and thus the detection signal V2 decreases. In order to quantify (i.e., digitalize) the detection signal V2 based on this eddy current, focus is placed on an amplitude value Y that is a value indicative of the magnitude of the detection signal V2, and a value X (=Y cos Φ) that is a value attributed to the phase difference Φ of the detection signal V2 with respect to the AC excitation signal V1, as shown in FIG. 3. As a result, the following becomes evident.

First, there is a correlation between the amplitude value Y of the detection signal V2 and the hardened surface hardness (i.e., the hardness of the portion that has been hardened). That is, there is a relationship in which the magnetic permeability is high when the hardened surface hardness is low, as is evident from comparing the hardness change curve 4 and the magnetic permeability change curve 5 in FIG. 1. When the magnetic permeability is high, the magnetic flux generated when the AC excitation signal V1 is applied to the exciting coil 7 increases, so the eddy current induced at the surface of the measured portion 6a also increases. As a result, the amplitude value Y of the detection signal V2 detected by the detection coil 8 also increases. Therefore, conversely, the magnetic flux that is generated by the eddy current and penetrates the measured portion 6a, i.e., the magnetic permeability, can be derived from the amplitude value Y of the detection signal V2 detected by the detection coil 8. Accordingly, the hardened surface hardness can be obtained from the relationship between the hardness change curve 4 and the magnetic permeability change curve 5 shown in FIG. 1.

Next, there is a correlation between the value X that is attributed to the phase difference Φ of the detection signal V2 with respect to the AC excitation signal V1, and the hardening depth (i.e., the depth of the hardened layer). That is, as the hardening depth increases, i.e., as the hardened layer 1 that has been hardened, of the hardened member, increases, the low range of the magnetic permeability increases in the depth direction, and the phase delay of the detection signal V2 with respect to the AC excitation signal V1 increases. As a result, the hardening depth is obtained from the size of the value that is attributed to the phase difference Φ.

In eddy current measuring to inspect the hardening quality of a hardened component according to a measurement principle such as that described above, an eddy current measuring sensor that has an exciting coil and a detection coil is used, as described above. Hereinafter, the structure of the eddy current measuring sensor according to embodiments of the invention will be described.

Figure 4:
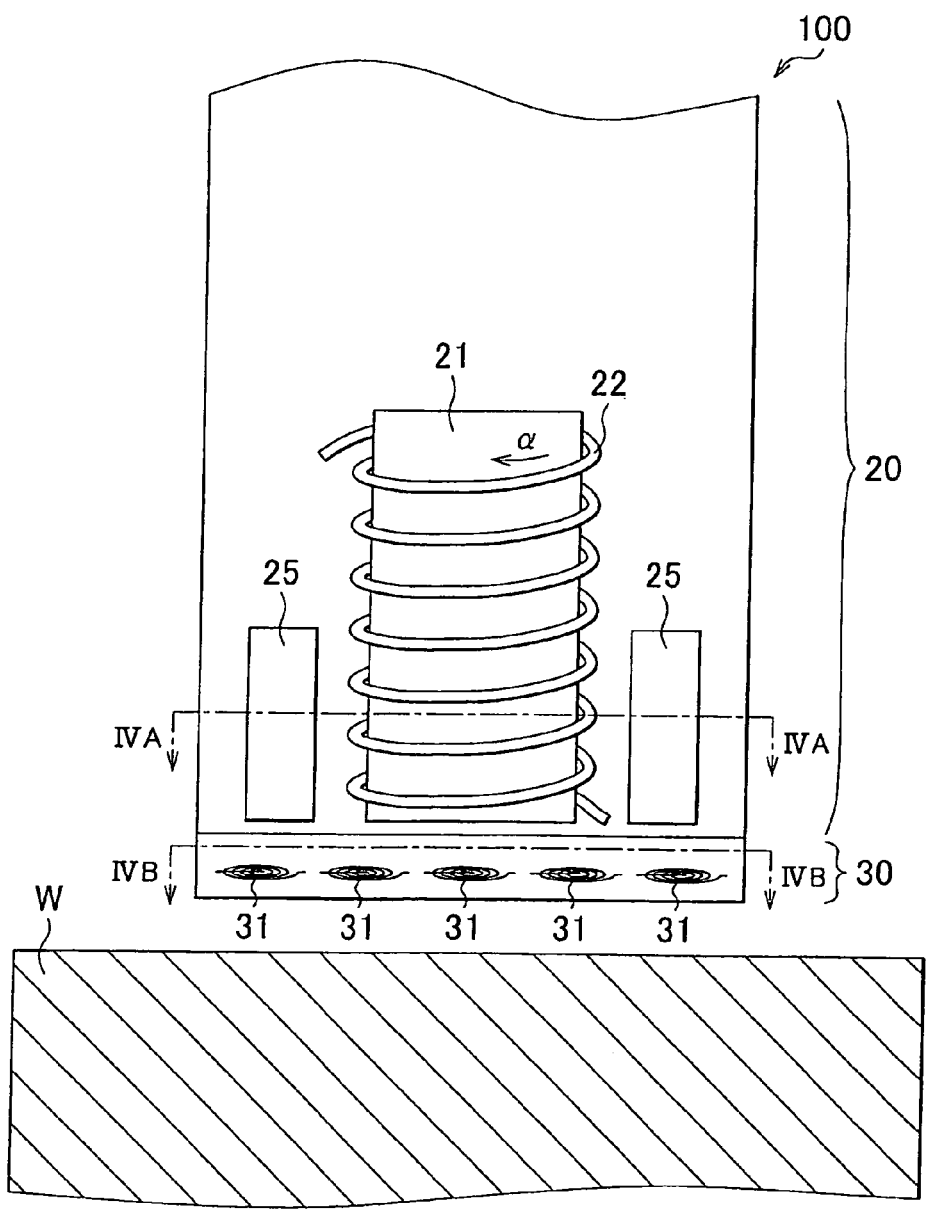
FIG. 4 is a schematic diagram of the structure of an eddy current measuring sensor according to a first embodiment of the invention.

First, an eddy current measuring sensor 100 according to a first embodiment of the invention will be described with reference to FIGS. 4 to 10. Incidentally, in this specification, the upper side in FIG. 4 will be referred to as up, the lower side in FIG. 4 will be referred to as down, the right side in FIG. 4 will be referred to as the right, and the left side in FIG. 4 will be referred to as the left. Moreover, the side toward the surface of the paper on which FIG. 4 is drawn will be referred to as the front, and the side away from the surface in the depth direction of the paper on which FIG. 4 is drawn will be referred to as the back. Also, to simplify the description, in FIGS. 4 and 6 to 10, only the sub-cores 25 on the left and right ends are shown; all of the other sub-cores 25 are omitted.

As shown in FIGS. 4 and 5, the eddy current measuring probe sensor 100 according to this embodiment has an exciting portion 20 and a detecting portion 30. The exciting portion 20 applies a predetermined AC excitation signal (i.e., the AC excitation signal V1) to a work W which is the component to be measured, as described above. The detecting portion 30 detects a detection signal (i.e., the detection signal V2) as induced voltage that is induced by the magnetic field generated by an eddy current, from the work W to which the AC excitation signal is applied.

The exciting portion 20 includes a primary exciting portion and a secondary exciting portion. The primary exciting portion includes a cylindrical main core 21 formed of magnetic material with high magnetic permeability such as ferrite or permalloy, and a main coil 22 that is a solenoid coil wound in the circumferential direction around the main coil 21. Also, both ends (i.e., both terminals) of the main coil 22 are connected to an AC power supply, not shown. That is, the main coil 22 is an exciting coil for applying a predetermined AC excitation signal to the work W, and the main core 21 intensifies the magnetic field generated by the main coil 22.

Figure 5A:
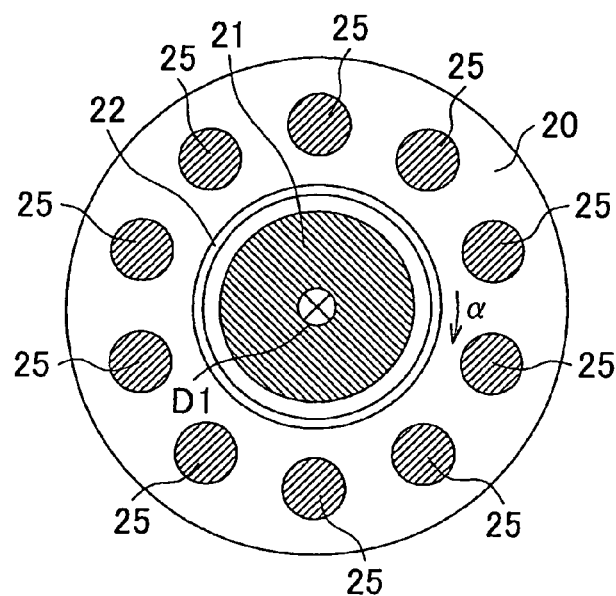
FIG. 5A is a sectional diagram taken along line IVA-IVA in FIG. 4.

Meanwhile, the secondary exciting portion includes cylindrical sub-cores 25 arranged around the main core 21 and the main coil 22 that form the primary exciting portion, with the axial direction of each of the sub-cores 25 being the same as the axial direction of the main core 21. The sub-cores 25 are made of magnetic material with high magnetic permeability such as ferrite or permalloy. In this embodiment, ten of these sub-cores 25 are arranged around the primary exciting portion as shown in FIG. 5A, but the number of sub-cores 25 is not limited to ten.

The main core 21, the main coil 22, and each of the sub-cores 25 are each arranged at the tip ends of separate rods, not shown, that extend in the tip end direction (i.e., in the direction toward the work W side) of the eddy current measuring sensor 100, inside the exciting portion 20. Each of the rods is able to slide in the axial direction inside the eddy current measuring sensor 100. That is, the main core 21, the main coil 22, and each of the sub-cores 25 are each able to change position independently relative to one another in the axial direction in the exciting portion 20 (see FIGS. 6 to 10).

Figure 5B:
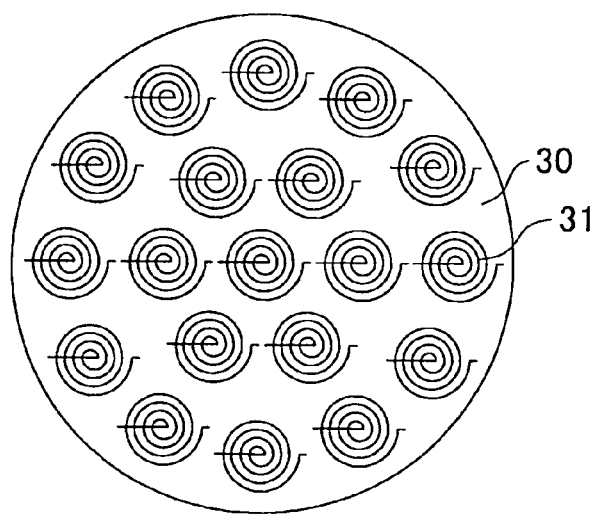
FIG. 5B is a sectional diagram taken along line IVB-IVB in FIG. 4.

The detecting portion 30 includes a plurality of detection coils 31 that are pancake coils arranged over the entire tip end surface (the surface on the side of the work W) of the exciting portion 20, as shown in FIG. 5B. Also, each of the detection coils 31 is connected at both ends (i.e., at both terminals) to a measuring device, not shown. That is, each detection coil 31 generates a detection signal as induced voltage that is induced by the magnetic field generated by the eddy current from the work W to which the AC excitation signal is applied (hereinafter this signal will also simply be referred to as a "detection signal"). Incidentally, in this embodiment, pancake coils are used as the detection coils 31, but planar coils may also be used.

When performing an eddy current measurement using the eddy current measuring sensor 100 structured as described above, voltage is applied to the main coil 22 by the AC power supply. The instant current flows as shown by arrow α in FIGS. 4 and 5A through the main coil 22, a downward (i.e., in the direction toward the work W side) magnetic field is generated inside the main coil 22 (see arrow a11 in FIG. 6) according to the right-hand screw rule. Here, in FIG. 5A, the portion of the main core 21 denoted by reference character D1 is a marked portion indicating the direction of the magnetic field in the vertical direction according to the main coil 22. The reference character D1 is a mark indicating that the magnetic field in the vertical direction is headed toward the back of the paper on which FIG. 5A is drawn, with respect to the surface of paper on which FIG. 5 is drawn.

The magnetic field generated as described above causes electromagnetic induction, which in turn generates an eddy current in the work W that is a magnetic body. Furthermore, with the generation of the eddy current at the surface of the work W, the magnetic flux penetrates the detection coils 31, thus producing induced voltage in the detection coils 31. This induced voltage is then measured by the detection coils 31.

A first example applied to an eddy current measurement performed during normal operation when an eddy current measurement is performed using the eddy current measuring sensor 100 according to the first embodiment will now be described. In this example, the eddy current measurement is performed while the main core 21 and the main coil 22 are moved to the tip end side of the eddy current measuring sensor 100, and the sub-cores 25 are moved to the side opposite the tip end of the eddy current measuring sensor 100 (i.e., toward the base end side, i.e., away from the work W), such that the sub-cores 25 are separated from the main core 21 and the main coil 22, as shown in FIG. 6.

Figure 6:
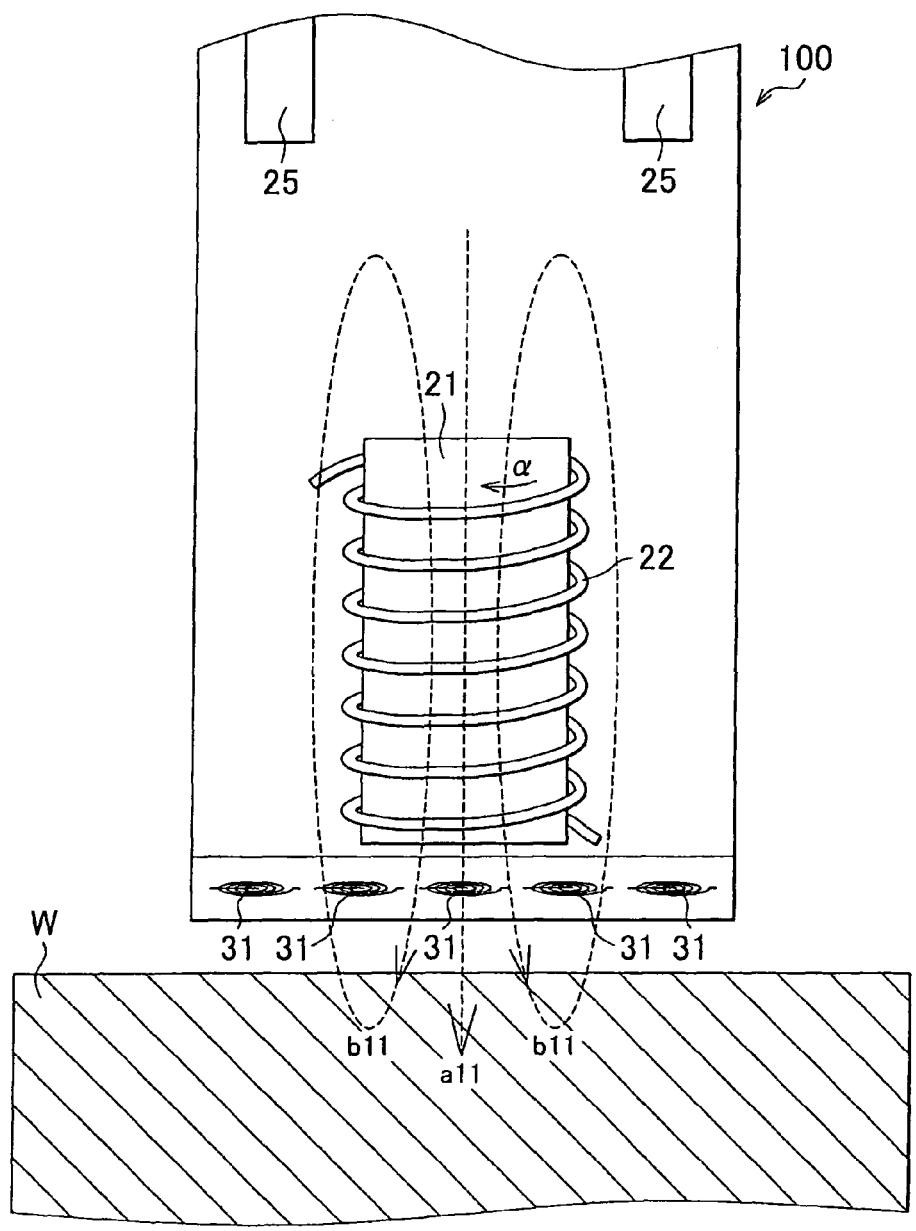
FIG. 6 is a schematic diagram of a first example of the eddy current measuring sensor according to the first embodiment.

In this example, the instant that current flows as shown by arrow α in FIG. 6 through the main coil 22, a downward magnetic field (arrow a11 in FIG. 6) is generated inside the main coil 22 according to the right-hand screw rule, and further, an upward magnetic field is generated outside the main coil 22. More specifically, a rotating magnetic field (arrow b11 in FIG. 6) that circulates around the main coil 22, i.e., that flows alternately inside and outside the main coil 22, is generated.

The eddy current produced as a result of the rotating magnetic field and the magnetic field in the vertical direction generated at the main coil 22 acting on the work W in this way is detected by the detection coils 31. In this way, in this example, performing an eddy current measurement as described above enables the eddy current to be measured without the measurement being affected by the sub-cores 25.

Next, a second example applied to an eddy current measurement performed while the magnetic field is widened all around when an eddy current measurement is performed using the eddy current measuring sensor 100 according to the first embodiment will now be described. In this example, the eddy current measurement is performed as described above while the main core 21, the main coil 22, and the sub-cores 25 are moved to the tip end side (i.e., in the direction toward the work W side) of the eddy current measuring sensor 100, as shown in FIG. 7.

Figure 7:
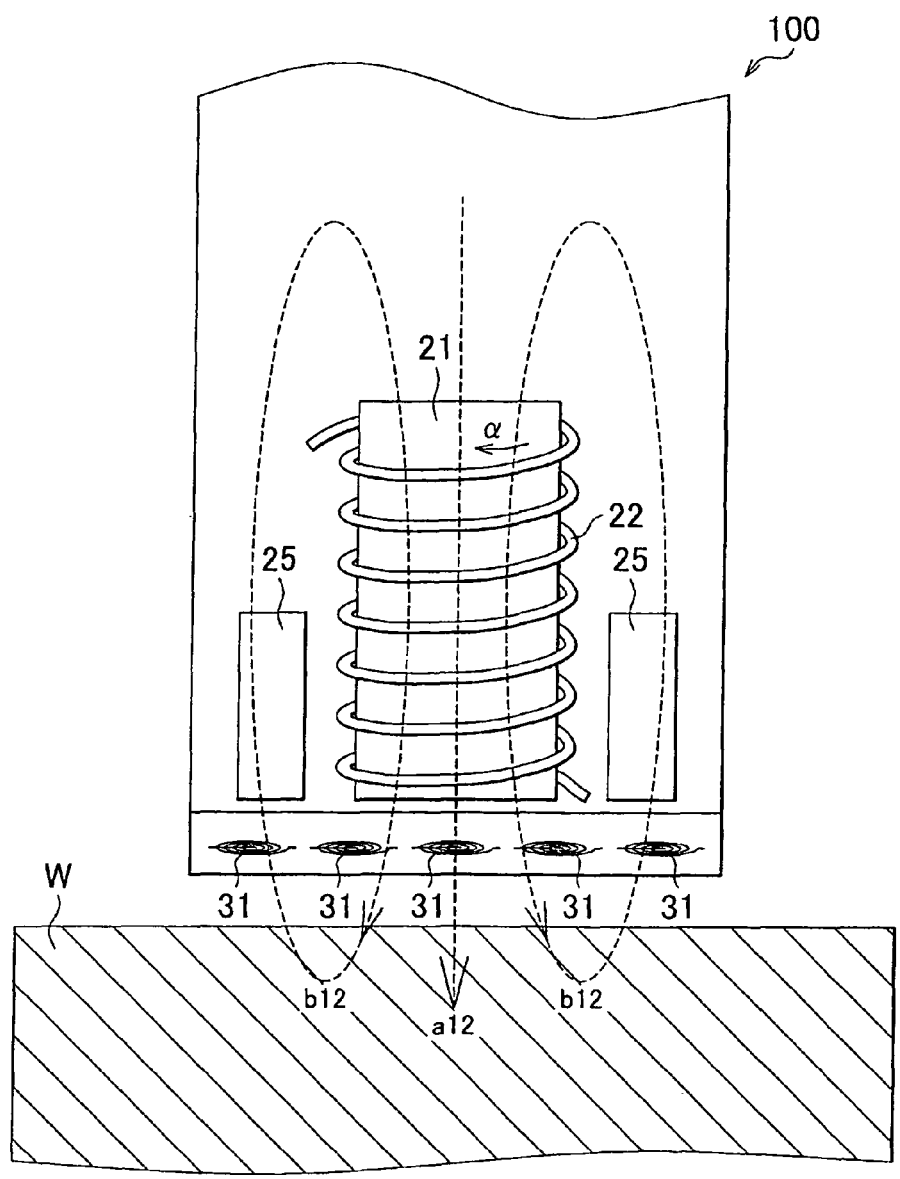
FIG. 7 is a schematic diagram of a second example of the eddy current measuring sensor according to the first embodiment.

In this example, the instant that current flows as shown by arrow α in FIG. 7 through the main coil 22, a downward magnetic field (arrow a12 in FIG. 7) is generated inside the main coil 22 according to the right-hand screw rule, and further, a rotating magnetic field (arrow b12 in FIG. 7) that circulates around the main coil 22, i.e., that flows alternately inside and outside the main coil 22, is generated.

At this time, the upward magnetic field outside the main coil 22 is attracted by the sub-cores 25 that have high magnetic permeability and thus expands outward. Therefore, the range of the rotating magnetic field that acts on the work W by the main coil 22 can be made even wider than it is in the first example, as shown in FIG. 7. In this way, the range of the rotating magnetic field generated at the main coil 22 can be expanded, so the eddy current generated by the rotating magnetic field acting on the work W can be expanded. Also, the eddy current of a wider area can be detected by the detection coils 31. In this way, in this example, performing an eddy current measurement as described above enables the eddy current to be measured while the magnetic field is widened all around at the work W by the sub-cores 25.

Next, a third example applied to an eddy current measurement performed while the magnetic field is intensified at the outside when an eddy current measurement is performed using the eddy current measuring sensor 100 according to the first embodiment will now be described. In this example, the eddy current measurement is performed as described above while the main coil 22 and the sub-cores 25 are moved to the tip end side of the eddy current measuring sensor 100, and the main core 21 is moved slightly to the base end side of the eddy current measuring sensor 100 with respect to the main coil 22, as shown in FIG. 8.

Figure 8:
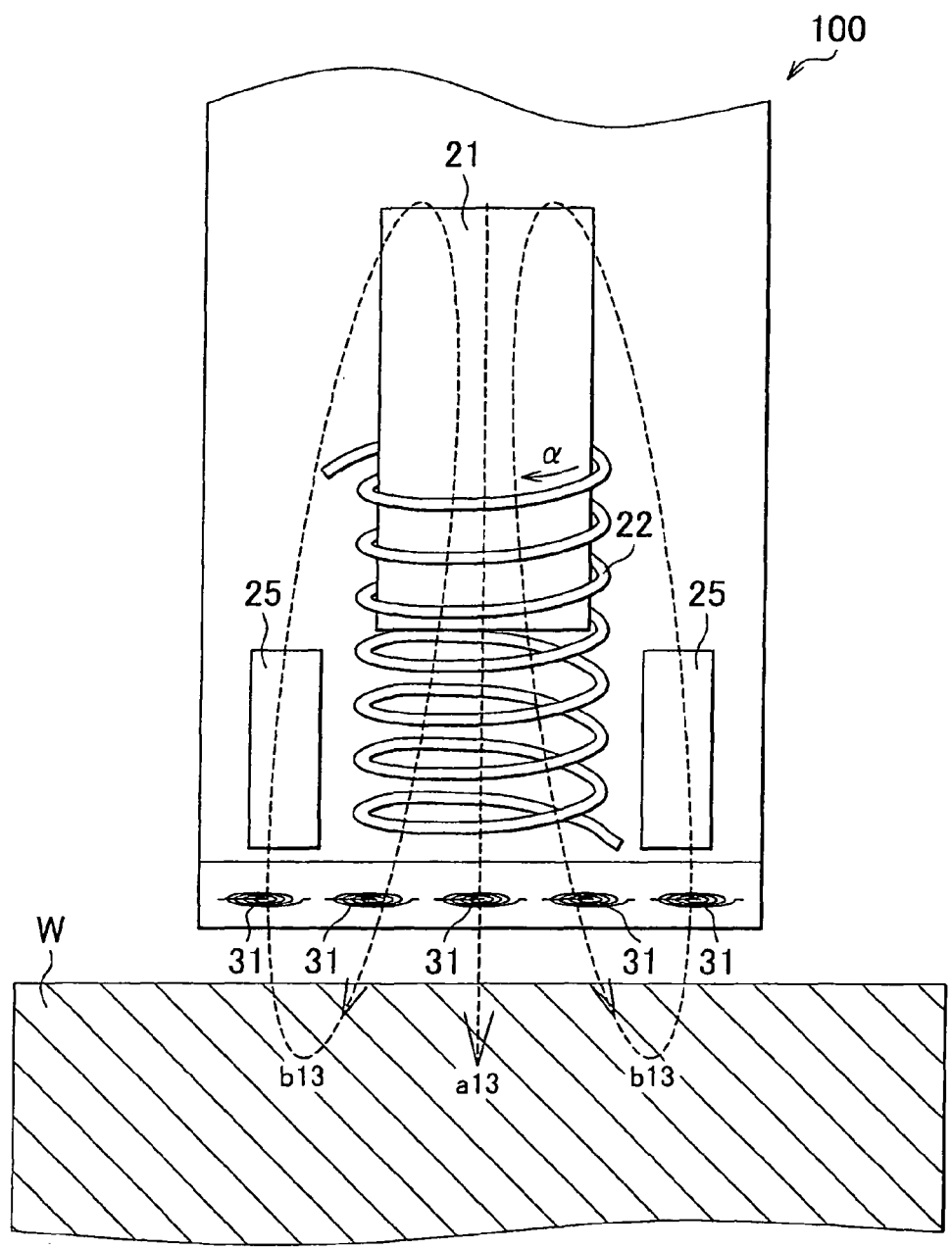
FIG. 8 is a schematic diagram of a third example of the eddy current measuring sensor according to the first embodiment.

In this example, the instant that current flows as shown by arrow α in FIG. 8 through the main coil 22, a downward magnetic field (arrow a13 in FIG. 8) is generated inside the main coil 22 according to the right-hand screw rule, and further, a rotating magnetic field (arrow b13 in FIG. 8) that circulates around the main coil 22, i.e., that flows alternately inside and outside the main coil 22, is generated.

At this time, the upward magnetic field outside the main coil 22 is attracted by the sub-cores 25, and at the same time, it is also attracted to the main core 21 that has moved to the upper side. Therefore, a rotating magnetic field is generated in a shape similar to that of a tube having a diameter that gradually increases from the upper side to the lower side, as shown in FIG. 8, and the rotating magnetic field that forms the increased diameter portion acts on the work W. Forming the rotating magnetic field generated at the main coil 22 in a shape similar to that of a tube having a larger diameter at the portion of the work W in this way intensifies the magnetic field at the work W at the outside, and thus enables the eddy current generated by the rotating magnetic field acting on the work W to be stronger at the outside. Then the eddy current at the outside is able to be selectively detected by the detection coils 31. In this way, in this example, performing an eddy current measurement as described above enables the eddy current to be measured while the magnetic field is intensified at the outside at the work W by the main core 21 and the sub-cores 25.

Next, a forth example applied to an eddy current measurement performed while the magnetic field is intensified at the inside center portion when an eddy current measurement is performed using the eddy current measuring sensor 100 according to the first embodiment will now be described. In this example, the eddy current measurement is performed as described above while the main core 21 is moved to the tip end side of the eddy current measuring sensor 100, the sub-cores 25 are moved to the base end side of the eddy current measuring sensor 100, and the main coil 22 is moved to an intermediate position with respect to the main core 21 and the sub-cores 25, as shown in FIG. 9.

In this example, the instant that current flows as shown by arrow α in FIG. 9 through the main coil 22, a downward magnetic field (arrow a14 in FIG. 9) is generated inside the main coil 22 according to the right-hand screw rule, and further, a rotating magnetic field (arrow b14 in FIG. 9) that circulates around the main coil 22, i.e., that flows alternately inside and outside the main coil 22, is generated.

At this time, an upward magnetic field outside the main coil 22 is attracted by the sub-cores 25, and at the same time, a downward magnetic field inside the main coil 22 is attracted to the main core 21. Therefore, a rotating magnetic field is generated in a shape similar to that of a tube having a diameter that gradually decreases from the upper side to the lower side, as shown in FIG. 9, and the rotating magnetic field that forms the decreased diameter portion acts on the work W. Forming the rotating magnetic field generated at the main coil 22 in a shape similar to that of a tube having a smaller diameter at the portion of the work W in this way intensifies the magnetic field at the work W at the inside center portion, and thus enables the eddy current generated by the rotating magnetic field acting on the work W to be stronger at the inside center portion. Then the eddy current at the inside center portion is able to be selectively detected by the detection coils 31. In this way, in this example, performing an eddy current measurement as described above enables the eddy current to be measured while the magnetic field is intensified at the inside center portion of the work W by the main core 21 and the sub-cores 25.

Next, a fifth example applied to an eddy current measurement performed while the magnetic field is intensified on one side when an eddy current measurement is performed using the eddy current measuring sensor 100 according to the first embodiment will now be described. In this example, the eddy current measurement is performed as described above while the main core 21 and the main coil 22 are moved to the tip end side of the eddy current measuring sensor 100, one of the sub-cores 25 (i.e., the sub-core 25 on the left side in FIG. 10) is moved to the tip end side of the eddy current measuring sensor 100, and the other sub-core 25 (i.e., the sub-core 25 on the right side in FIG. 10) is moved to the base end side of the eddy current measuring sensor 100, such that the other sub-core 25 is separated from the main core 21 and the main coil 22, as shown in FIG. 10.

Figure 10:
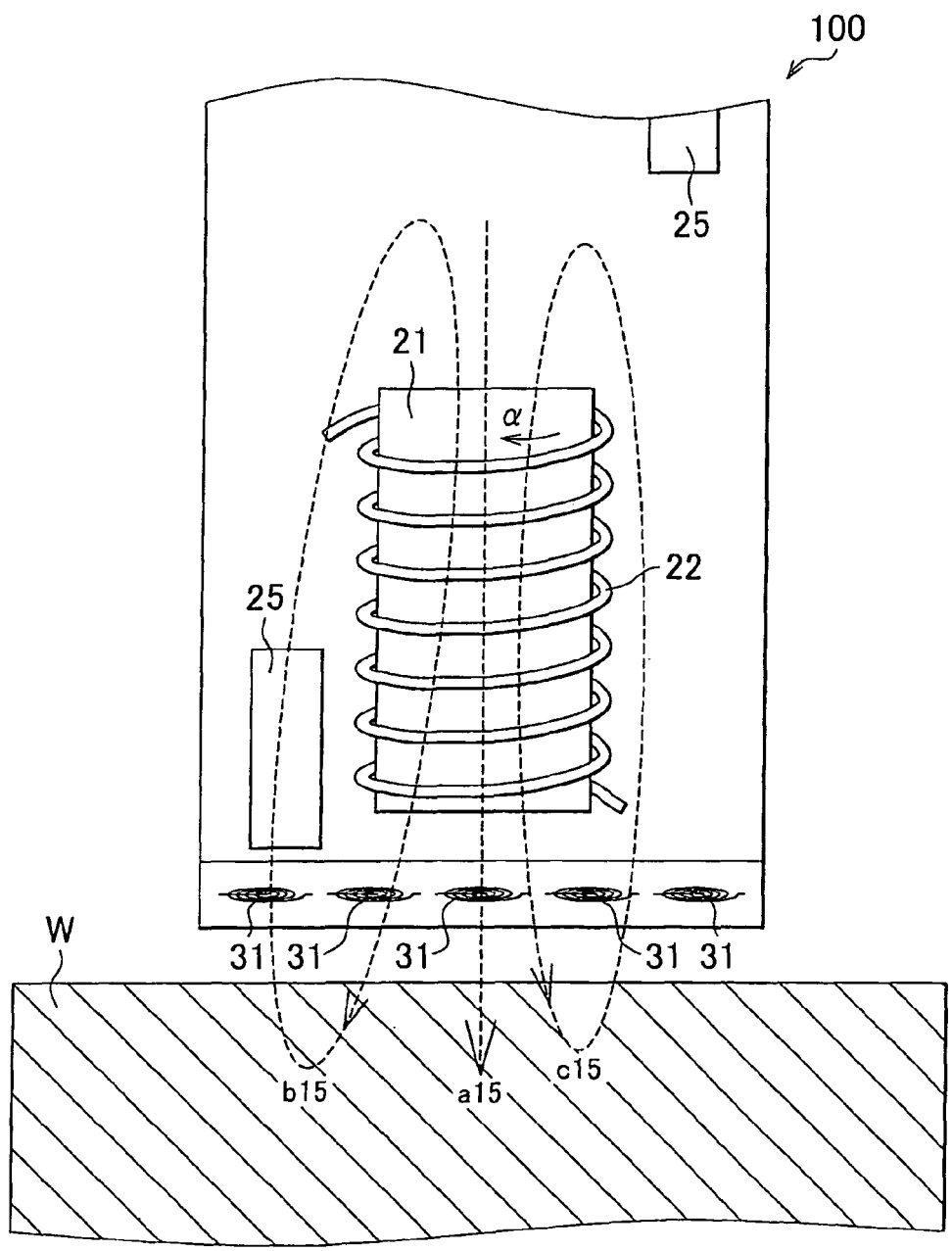
FIG. 10 is a schematic diagram of a fifth example of the eddy current measuring sensor according to the first embodiment.

In this example, the instant that current flows as shown by arrow α in FIG. 10 through the main coil 22, a downward magnetic field (arrow a15 in FIG. 10) is generated inside the main coil 22 according to the right-hand screw rule, and further, a rotating magnetic field (arrows b15 and c15 in FIG. 10) that circulates around the main coil 22, i.e., that flows alternately inside and outside the main coil 22, is generated.

At this time, the upward magnetic field on the right side outside the main coil 22 is not affected by the sub-core 25 on the upper right side, so a normal magnetic field is generated. On the other hand, the upward magnetic field on the left side outside the main coil 22 is attracted by the sub-core 25, so a rotating magnetic field on the left side outside the main coil 22 is generated in a shape that is progressively offset to the left side from the upper side toward the lower side as shown in FIG. 10, and the rotating magnetic field of the portion offset to the left acts on the work W. Having the shape of the rotating magnetic field generated at the main coil 22 be offset to the left at the portion of the work W on one side, and thug enables the eddy current generated by the rotating magnetic field acting on the work W to be stronger on one side. Then the eddy current on one side is able to be selectively detected by the detection coils 31. In this way, in this example, performing an eddy current measurement as described above enables the eddy current to be measured while the magnetic field is intensified on one side of the work W by the sub-core 25.

The exciting portion 20 of the eddy current measuring sensor 100 according to the embodiment described above includes the main core 21 and the main coil 22 which together serve as the primary exciting portion, and the cylindrical sub-cores 25 arranged around the primary exciting portion with the axial direction of the sub-cores 25 being the same as the axial direction of the main core 21. Also, the main core 21, the main coil 22, and each of the sub cores 25 are each able to independently change position relative to each other in the axial direction in the exciting portion 20.

In this embodiment, the rotating magnetic field that circulates around the main coil 22, i.e., that flows alternately inside and outside the main coil 22, can be changed as necessary by mutually changing the positional relationships among the main core 21, the main coil 22, and the sub-cores 25, as described above. That is, the magnetic field at the work W can be widened or offset to one side, so the spread and direction and the like of the magnetic field can be controlled appropriately.

Also, the detecting portion 30 of the eddy current measuring sensor 100 according to this embodiment includes the plurality of detection coils 31 that are pancake coils arranged over the entire tip end surface of the exciting portion 20. In this embodiment, the structure described above enables the magnetic field in the vertical direction and the magnetic field in the horizontal direction at the tip end surface of the eddy current measuring sensor 100 to be detected and evaluated uniformly with the same sensitivity. Also, having the width of the detecting portion 30 be smaller enables the distance between the exciting portion 20 and the work W to be smaller, so the accuracy of the eddy current measurement can be improved.

Next, an eddy current measuring sensor 200 according to a second embodiment of the invention will be described with reference to FIGS. 11 to 15. Incidentally, portions in the description of the eddy current measuring sensor in the embodiment described below that are common to portions in the embodiment described above will be denoted by like reference characters and descriptions of those portions will be omitted. Also, to simplify the description, in FIGS. 11, 13, and 14, only the sub-cores 25 and sub-coils 26 on the left and right ends are shown; all of the other sub-cores 25 and sub-coils 26 are omitted.

Figure 11:
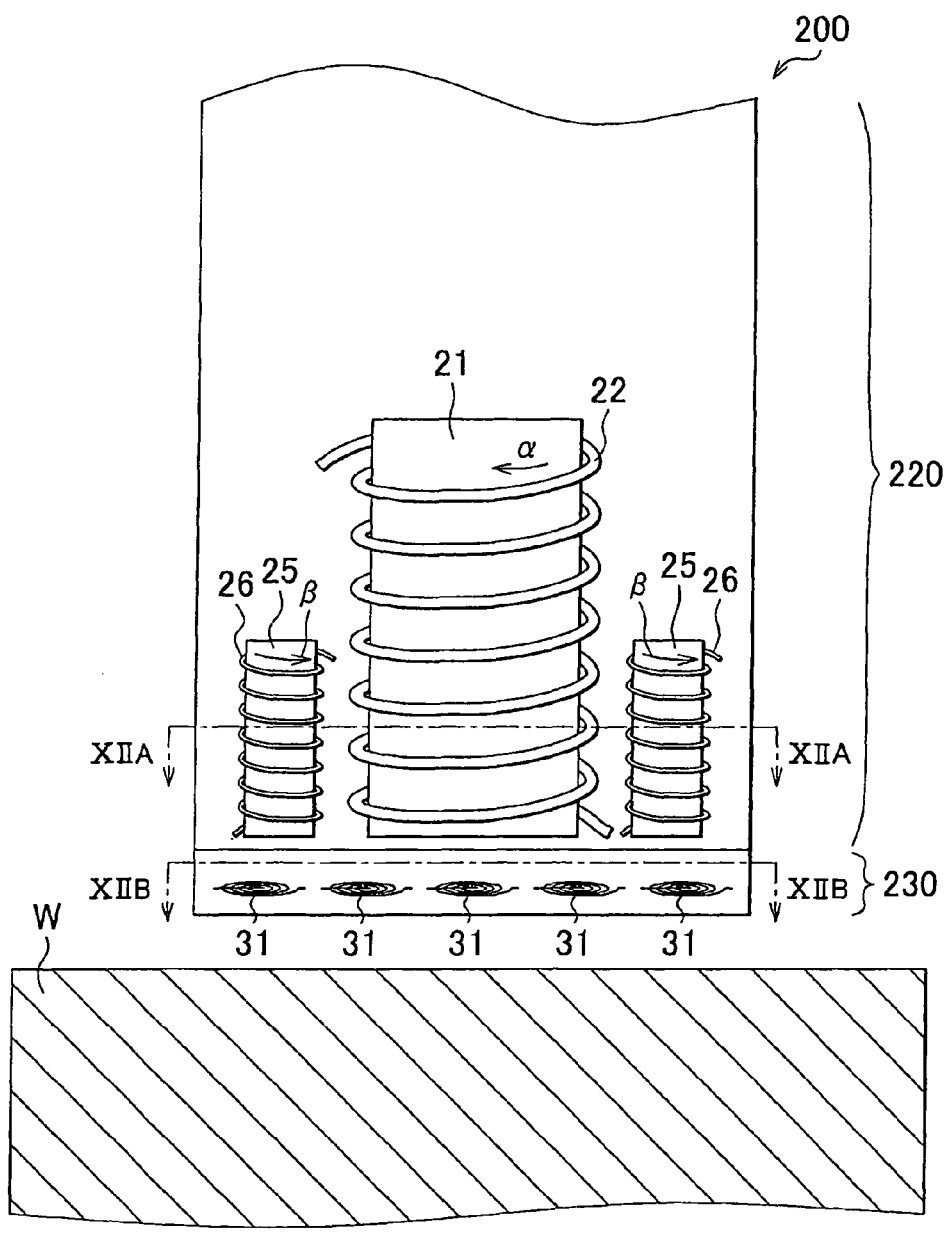
FIG. 11 is a schematic diagram of the structure of an eddy current measuring sensor according to a second embodiment of the invention.

As shown in FIGS. 11 and 12, the eddy current measuring probe sensor 200 according to this embodiment has an exciting portion 220 and a detecting portion 230, similar to the first embodiment described above. The exciting portion 220 applies a predetermined AC excitation signal to a work W that is the component to be measured, and the detecting portion 230 detects a detection signal by an eddy current from the work W to which the AC excitation signal is applied.

The exciting portion 220 includes a primary exciting portion and a secondary exciting portion. The primary exciting portion includes a cylindrical main core 21 made of magnetic material such as ferrite or permalloy, and a main coil 22 that is a solenoid coil wound in the circumferential direction around the main coil 21.

Meanwhile, the secondary exciting portion includes cylindrical sub-cores 25 and sub-coils 26. The sub-cores 25 are made of magnetic material such as ferrite or permalloy and are arranged around the main core 21 and the main coil 22 that form the primary exciting portion, with the axial direction of each of the sub-cores 25 being the same as the axial direction of the main core 21. The sub-coils 26 are solenoid coils that are wound in the circumferential direction around the sub-cores 25.

Also, both ends (i.e., both terminals) of the main coil 22 and the sub-coils 26 are connected to an AC power supply, not shown. That is, the main coil 22 and the sub-coils 26 are exciting coils for applying a predetermined AC excitation signal to the work W, and the main core 21 and the sub-cores 25 intensify the magnetic fields generated by the main coil 22 and the sub-coils 26, respectively. Also, the AC power supply applies voltage independently to each of the sub-coils 26. That is, the AC power supply is configured to switch the current to each the sub-coils 26 on or off according to the state of the magnetic field applied to the work W.

The main core 21, the main coil 22, and the sub-cores 25 are each able to independently change position relative to each other in the axial direction in the exciting portion 220, similar to the embodiment described above. Incidentally, the sub-coils 26 are unable to change position relative to the sub-cores 25.

Figure 12A:
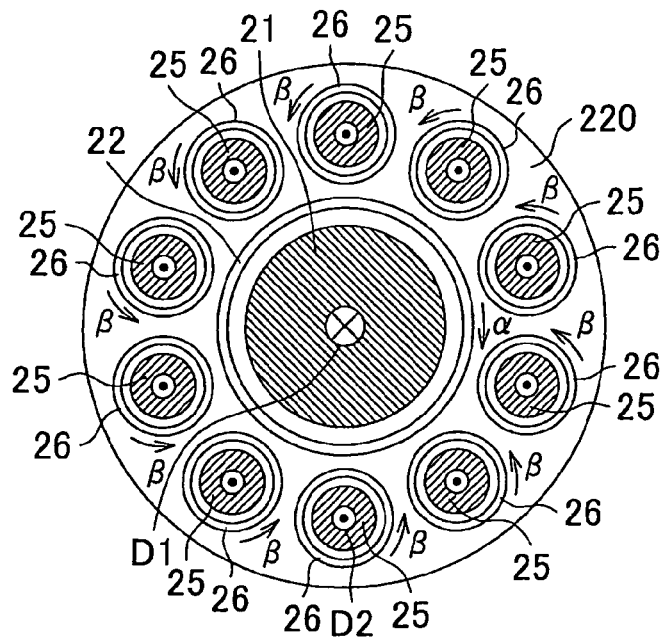
FIG. 12A is a sectional diagram taken along line. XIIA-XIIA in FIG. 11.
Figure 12B:
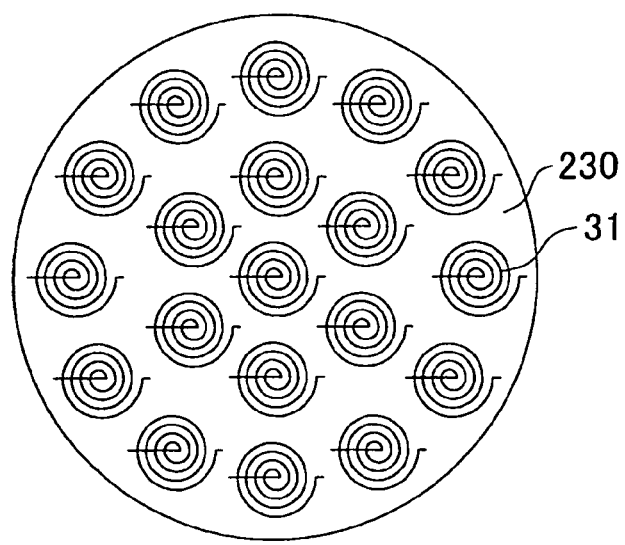
FIG. 12B is a sectional diagram taken along line XIIB-XIIB in FIG. 11.

The detecting portion 230 includes a plurality of detection coils 31 that are pancake coils arranged over the entire tip end surface of the exciting portion 220, as shown in FIG. 12B. Also, each of the detection coils 31 is connected at both ends (i.e., at both terminals) to a measuring device, not shown.

When performing an eddy current measurement using the eddy current measuring sensor 200 structured as described above, voltage is applied to the main coil 22 and the sub-coils 26 by the AC power supply. At this time, the voltage is applied such that the direction of the magnetic flux generated by the main coil 22 of the primary exciting portion (i.e., the direction of the magnetic flux that penetrates the main core 21) is opposite the direction of the magnetic flux generated by the sub-coils 26 of the secondary exciting portion (i.e., the direction of the magnetic flux that penetrates the sub-cores 25). More specifically, as shown in FIGS. 11 and 12A, the instant current flows as shown by arrow α clockwise through the main coil 22 when viewed from above, current flows as shown by arrow β counterclockwise through the sub-coils 26 when viewed from above.

Figure 13:
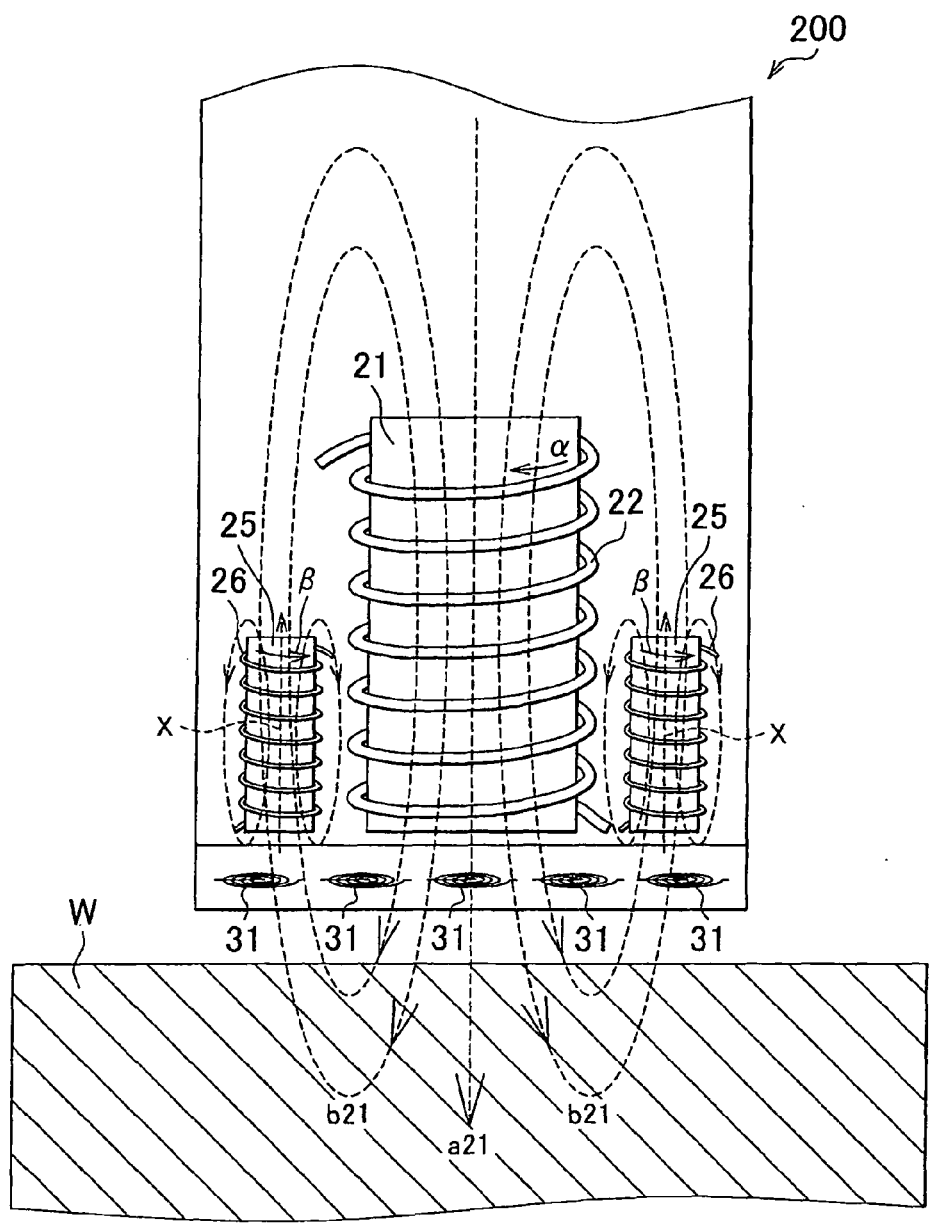
FIG. 13 is a schematic diagram of a first example of the eddy current measuring sensor according to the second embodiment.

The instant current flows as shown by arrow α in FIGS. 11 and 12A through the main coil 22, a downward (i.e., in the direction toward the work W side) magnetic field is generated inside the main coil 22 according to the right-hand screw rule (see arrow a21 in FIG. 13). Also, the instant current flows as shown by arrow β in FIGS. 11 and 12A through the sub-coils 26, an upward magnetic field is generated inside the sub-coils 26 according to the right-hand screw rule (see arrow x in FIG. 13). Here, in FIG. 12A, the portion of the main core 21 denoted by reference character D1 is a marked portion indicating the direction of the magnetic field in the vertical direction according to the main coil 22. The reference character D1 is a mark indicating that the magnetic field in the vertical direction is headed toward the back of the paper of the paper on which FIG. 12A is drawn, with respect to the surface of paper on which FIG. 12A is drawn. Also, the portion of the sub-cores 25 indicated by reference character D2 is a marked portion indicating the direction of the magnetic field in the vertical direction. The reference character D2 is a mark indicating that the magnetic field in the vertical direction is headed toward the front of the paper on which FIG. 12A is drawn.

The magnetic field generated as described above causes electromagnetic induction, which in turn generates an eddy current in the work W that is a magnetic body. Furthermore, with the generation of the eddy current at the surface of the work W, magnetic flux penetrates the detection coils 31, thus producing induced voltage in the detection coils 31. This induced voltage is then measured by the detection coils 31.

A first example applied to an eddy current measurement performed while the magnetic field is widened all around when an eddy current measurement is performed using the eddy current measuring sensor 200 according to the second embodiment will now be described. In this example, the eddy current measurement is performed while the main core 21, the main coil 22, the sub-cores 25, and the sub-coils 26 are moved to the tip end side of the eddy current measuring sensor 200, as shown in FIG. 13.

In this example, the instant that current flows as shown by arrow α and arrow β in FIG. 13 through the main coil 22 and the sub-coils 26, a downward magnetic field (arrow a21 in FIG. 13) is generated inside the main coil 22 according to the right-hand screw rule, and further, an upward magnetic field is generated outside the main coil 22. More specifically, a rotating magnetic field (arrow b21 in FIG. 13) that circulates around the main coil 22, i.e., that flows alternately inside and outside the main coil 22, is generated. In addition, an upward magnetic field (arrow x in FIG. 13) is generated inside each of the sub-coils 26.

At this time, the upward magnetic field outside the main coil 22 duplicates the direction of the upward magnetic fields generated by the sub-coils 26, so the rotating magnetic field that acts on the work W can be made stronger. That is, a magnetic field that is stronger than the magnetic field in the first embodiment described above can be applied to the work W, so the eddy current generated by the rotating magnetic field acting on the work W can be increased. Then an even larger eddy current can be detected by the detection coils 31.

Also, similar to the second example of the first embodiment described above, the upward magnetic field outside the main coil 22 is attracted by the sub-coils 26 and thus expands outward. Therefore, the region of the rotating magnetic field that is generated by the main coil 22 and acts on the work W can be expanded. Expanding the region of the rotating magnetic field generated at the main coil 22 in this way enables the eddy current that is generated by the rotating magnetic field acting on the work W to be expanded. Then, an eddy current of a broad region can be detected by the detection coils 31. In this way, in this example, performing an eddy current measurement as described above enables the eddy current to be measured while the magnetic field is widened all around at the work W by the sub-cores 25.

Figure 14:
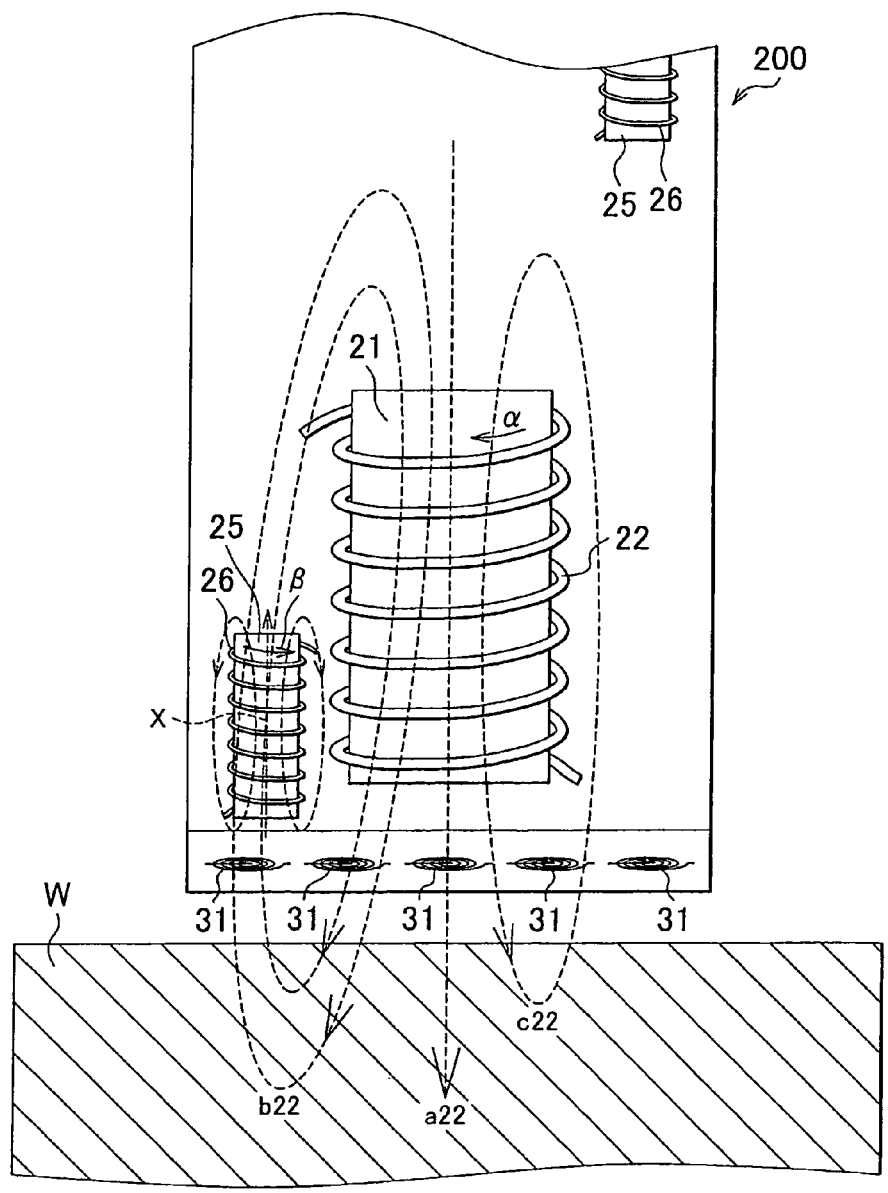
FIG. 14 is a schematic diagram of a second example of the eddy current measuring sensor according to the second embodiment.

Next, a second example applied to an eddy current measurement performed while the magnetic field is intensified on one side when an eddy current measurement is performed using the eddy current measuring sensor 200 according to the second embodiment will now be described. In this example, the eddy current measurement is performed while the main core 21 and the main coil 22 are moved to the tip end side of the eddy current measuring sensor 200, one of the sub-cores 25 and one of the sub-coils 26 (i.e., the sub-core 25 and the sub-coil 26 on the left side in FIG. 14) are moved to the tip end side of the eddy current measuring sensor 200, and the other of the sub-cores 25 and the other of the sub-coils 26 (i.e., the sub-core 25 and the sub-coil 26 on the right side in FIG. 14) are moved to the base end side of the eddy current measuring sensor 200, such that the other sub-core 25 and other sub-coil 26 are separated from the main core 21 and the main coil 22, as shown in FIG. 14. At this time, voltage is not applied to the sub-coil 26 that has been moved to the base end side.

In this example, the instant that current flows as shown by arrow α and arrow β in FIG. 14 through the main coil 22 and the sub-coils 26, a downward magnetic field (arrow a22 in FIG. 14) is generated inside the main coil 22 according to the right-hand screw rule, and further, an upward magnetic field is generated outside the main coil 22. More specifically, a rotating magnetic field (arrow b22 and arrow c22 in FIG. 14) that circulates around the main coil 22, i.e., that flows alternately inside and outside the main coil 22, is generated. In addition, an upward magnetic field (arrow x in FIG. 14) is generated inside the sub-coil 26 on the left side.

At this time, the upward magnetic field on the right side outside the main coil 22 is not affected by the sub-core 25 on the upper right side, so a normal magnetic field is generated. On the other hand, the upward magnetic field on the left side outside the main coil 22 duplicates the direction of the upward magnetic fields generated by the sub-coil 26, so the upward magnetic field on the left side outside the main coil 22 is intensified, and at the same time, is attracted by the sub-coil 26. Therefore, a rotating magnetic field on the left side outside the main coil 22 is generated in a shape that is progressively offset to the left side from the upper side toward the lower side as shown in FIG. 14, and the rotating magnetic field of the portion offset to the left acts strongly on the work W. Having the shape of the strong rotating magnetic field generated at the main coil 22 be offset to the left at the portion of the work W further intensifies the magnetic field at the work W on one side, and thus enables the eddy current generated by the rotating magnetic field acting on the work W to be stronger on one side. Then the eddy current on one side is able to be selectively detected by the detection coils 31. In this way, in this example, performing an eddy current measurement as described above enables the eddy current to be measured while the magnetic field is further intensified on one side of the work W by the sub-core 25 and the sub-coil 26.

Figure 15A:
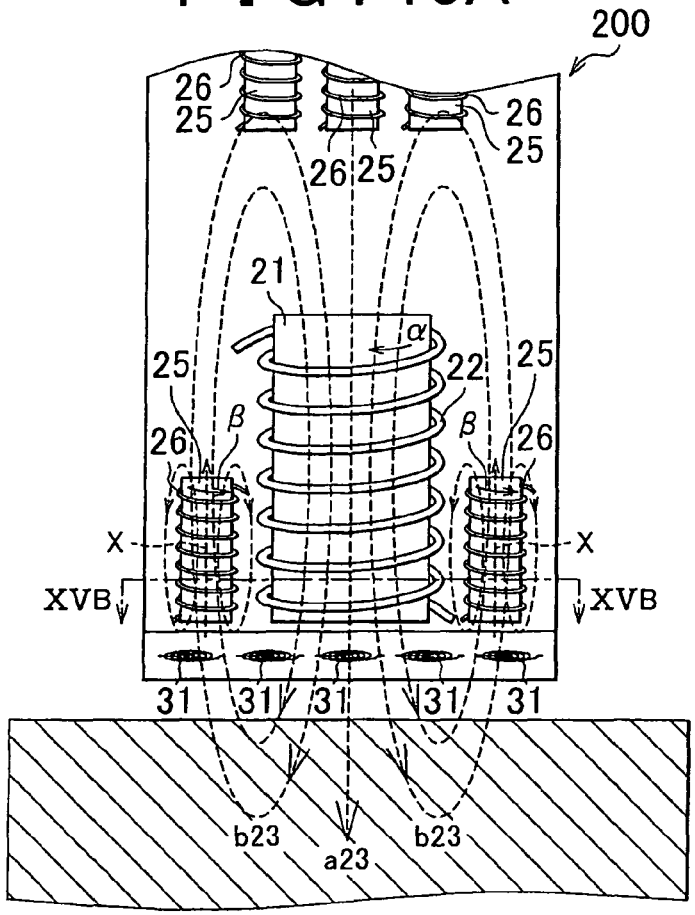
FIG. 15A is a sectional diagram of a third example of the eddy current measuring sensor according to the second embodiment.

Next, a third example applied to an eddy current measurement performed while the magnetic field at the work W is narrow in the front-back direction and wide in the left-right direction when an eddy current measurement is performed using the eddy current measuring sensor 200 according to the second embodiment will now be described. In this example, the eddy current measurement is performed while the main core 21 and the main coil 22 are moved to the tip end side of the eddy current measuring sensor 200, the sub-cores 25 and the sub-coils 26 on both the left and right ends are moved to the tip end side of the eddy current measuring sensor 200, and the sub-cores 25 and the sub-coils 26 that are in the front and back are moved to the base end side of the eddy current measuring sensor 200, such that the sub-cores 25 and the sub-coils 26 that are in the front and back are separated from the main core 21 and the main coil 22, as shown in FIG. 15. At this time, voltage is not applied to the sub-coils 26 that have been moved to the base end side.

In this example, the instant that current flows as shown by arrow α and arrow β in FIG. 15 through the main coil 22 and the sub-coils 26, a downward magnetic field (arrow a23 in FIG. 15) is generated inside the main coil 22 according to the right-hand screw rule, and further, an upward magnetic field is generated outside the main coil 22. More specifically, a rotating magnetic field (arrow b23 in FIG. 15) that circulates around the main coil 22, i.e., that flows alternately inside and outside the main coil 22, is generated. In addition, upward magnetic fields (arrows x in FIG. 15) are generated inside the sub-coils 26 on the left and right sides.

Figure 15B:
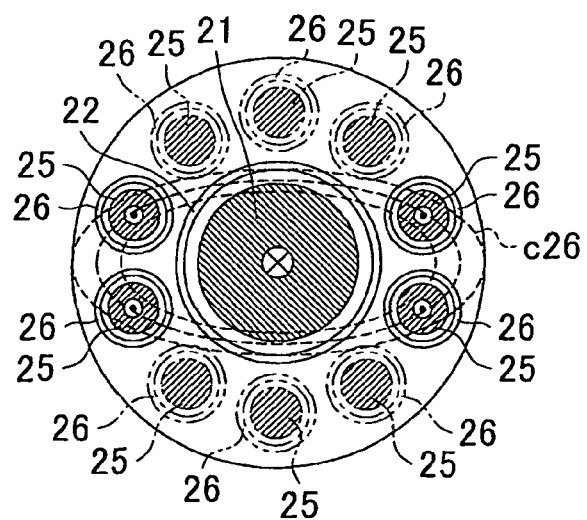
FIG. 15B is a sectional view taken along line XVB-XVB in FIG. 15A.

At this time, the upward magnetic field in back and front of the main coil 22 is not affected by the sub-cores 25 and the sub-coils 26 on the upper side, so normal magnetic field is generated. On the other hand, the upward magnetic field on the left and right sides outside the main coil 22 duplicates the direction of the upward magnetic fields generated by the sub-coils 26, so the upward magnetic field on the left and right sides outside the main coil 22 is intensified, and at the same time, is attracted by the sub-coils 26. Therefore, a rotating magnetic field on the left and right sides outside the main coil 22 is generated in a shape that is narrow in the front-back direction and wide in the left-right direction as shown in FIG. 15B, and the rotating magnetic field that is long in the left-right direction acts strongly on the work W. Having the shape of the strong rotating magnetic field generated at the main coil 22 be wide in the left-right direction at the portion of the work W in this way further intensifies the magnetic field at the work W in the left-right direction, and thus enables the eddy current generated by the rotating magnetic field acting on the work W to be stronger in the left-right direction. Then the eddy current in the left-right direction is able to be selectively detected by the detection coils 31. In this way, in this example, performing an eddy current measurement as described above enables the eddy current to be measured while the magnetic field is made narrow in the front-back direction and wider in the left-right direction at the work W by the sub-cores 25 and the sub-coils 26.

As described above, the exciting portion 220 of the eddy current measuring sensor 200 according to this embodiment includes the main core 21 and the main coil 22 that together serve as the primary exciting portion, and the cylindrical sub-cores 25 arranged around the primary exciting portion, with the axial direction of each of the sub-cores 25 being the same as the axial direction of the main core 21, and the sub-coils 26 that are solenoid coils wound in the circumferential direction around the sub-cores 25.

In this embodiment, according to the structure described above, the upward magnetic field outside the main coil 22 duplicates the direction of the upward magnetic fields generated by the sub-coils 26, thus making rotating magnetic field that acts on the work W stronger. That is, a magnetic field that is stronger than the magnetic field in the first embodiment described above is applied to the work W, so a larger eddy current is detected by the detection coils 31. In addition, the relative positions of the main core 21, the main coil 22, and the sub-cores 25 (i.e., the sub-coils 26) are changed. As a result, the magnetic field at the work W can be widened or offset to one side, so the spread and direction and the like of the magnetic field can be appropriately controlled. Incidentally, in this embodiment as well, the magnetic field can also be intensified toward the outside of the main core 21 or intensified toward the inside center portion, as in the first embodiment described above.

Next, an eddy current measuring sensor according to a third embodiment of the invention will be described with reference to FIGS. 16 to 19. Incidentally, to simplify the description, in FIGS. 16 and 18 to 19A only the sub-cores 25 and the sub-coils 26 on the left and right ends are shown; all of the other sub-cores 25 and sub-coils 26 are omitted.

Figure 16:
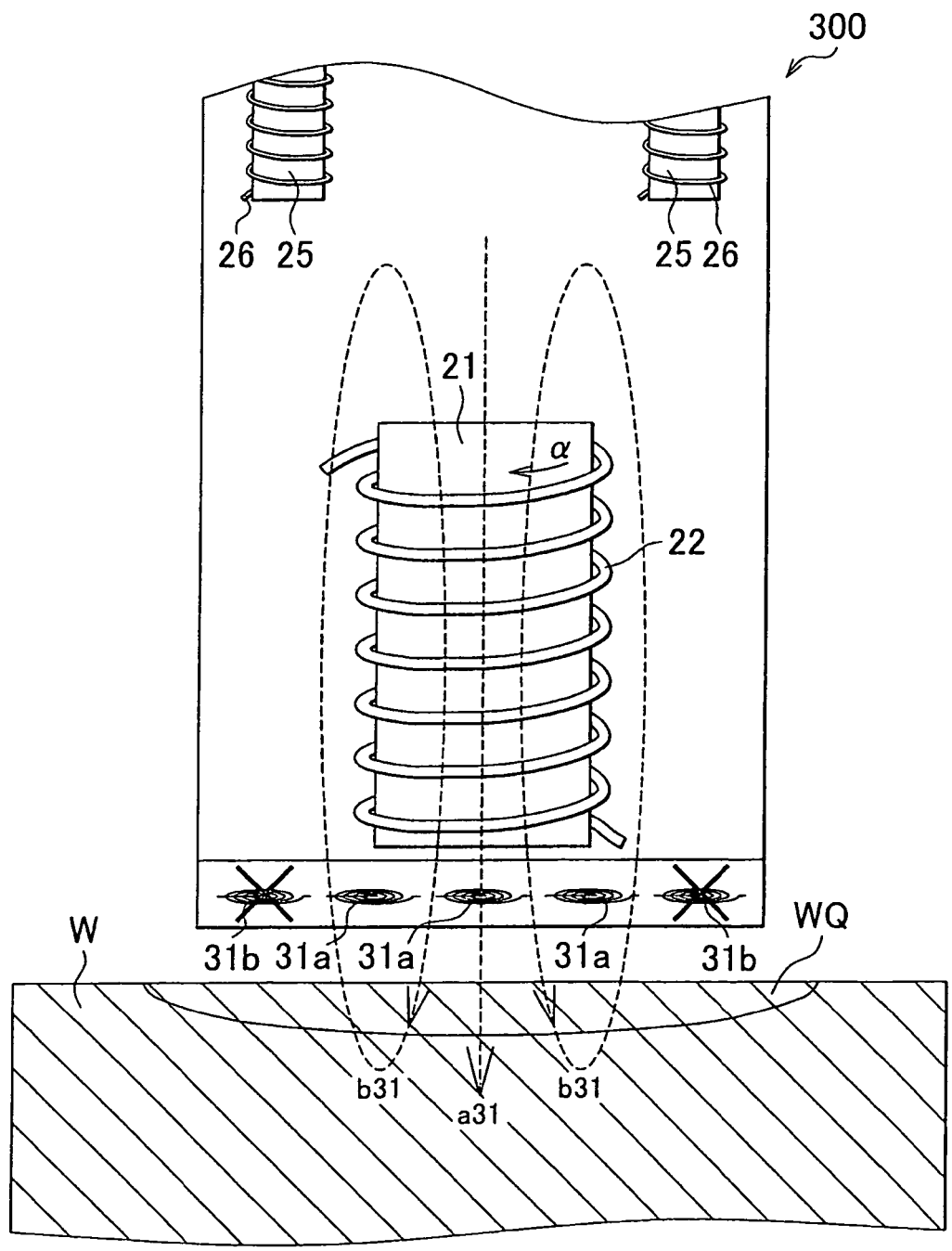
FIG. 16 is a schematic diagram of a first example of the eddy current measuring sensor according to a third embodiment of the invention.

As shown in FIG. 16, an eddy current measuring probe sensor 300 according to this embodiment has a plurality of detection coils 31 of which the detecting portions are arranged radially about an axial portion of a primary exciting portion, similar to the second embodiment described above. The detection coils 31 in this embodiment are formed of pancake coils, just as in the embodiment described above, but they may also be formed of solenoid coils that are wound around inside the main coil 22 and the sub-coils 26, for example.

Moreover, the detection coils 31 are each configured so as to be able to independently and selectively make a detection signal related to the detection of an eddy current generated in a work W so as to be acknowledged or ignored. More specifically, the detection coils 31 are controlled such that only detection signals from acknowledged detection coils 31a that make the detection signals so as to be acknowledged, from among the detection coils 31, are received by the measuring device 11, and detection signals from ignored detection coils 31b that make the detection signals so as to be ignored are not received by the measuring device 11.

A first example applied to an eddy current measurement performed during normal operation when measuring the hardening depth and the hardness of a hardened layer formed in steel using the eddy current measuring sensor 300 according to the third embodiment will now be described. In this example, an eddy current measurement such as that described above is performed while the main core 21 and the main coil 22 are moved to the tip end side of the eddy current measuring sensor 300, and the sub-cores 25 and the sub-coils 26 are moved to the base end side of the eddy current measuring sensor 300, such that the sub-cores 25 and the sub-coils 26 are separated from the main core 21 and the main coil 22, as shown in FIG. 16.

In this example, the instant that current flows as shown by arrow β in FIG. 16 through the main coil 22, a downward magnetic field (arrow a31 in FIG. 16) is generated inside the main coil 22 according to the right-hand screw rule, and further, an upward magnetic field is generated outside the main coil 22. More specifically, a rotating magnetic field (arrow b31 in FIG. 16) that circulates around the main coil 22, i.e., that flows alternately inside and outside the main coil 22, is generated.

The magnetic field in the vertical direction and the rotating magnetic field generated at the main coil 22 in this way act on the portion of a hardened layer WQ formed in the work W that is opposite the main coil 22 and generates an eddy current there, as shown in FIG. 16. In this example, the detection coils arranged opposite the portions where the eddy current is generated are the acknowledged detection coils 31a and the detection coils positioned at the other outer peripheral edge portions are the ignored detection coils 31b. The hardening depth and the hardness of the hardened layer WQ are measured by the acknowledged detection coils 31*a* based on only the signals that have detected the eddy current generated in the hardened layer WQ.

In this way, in this example, by performing an eddy current measurement as described above, the detection region can be selected freely by selectively making the detection signals of the detection coils so as to be acknowledged or ignored as appropriate for the spread and the direction of the magnetic field.

Figure 17:
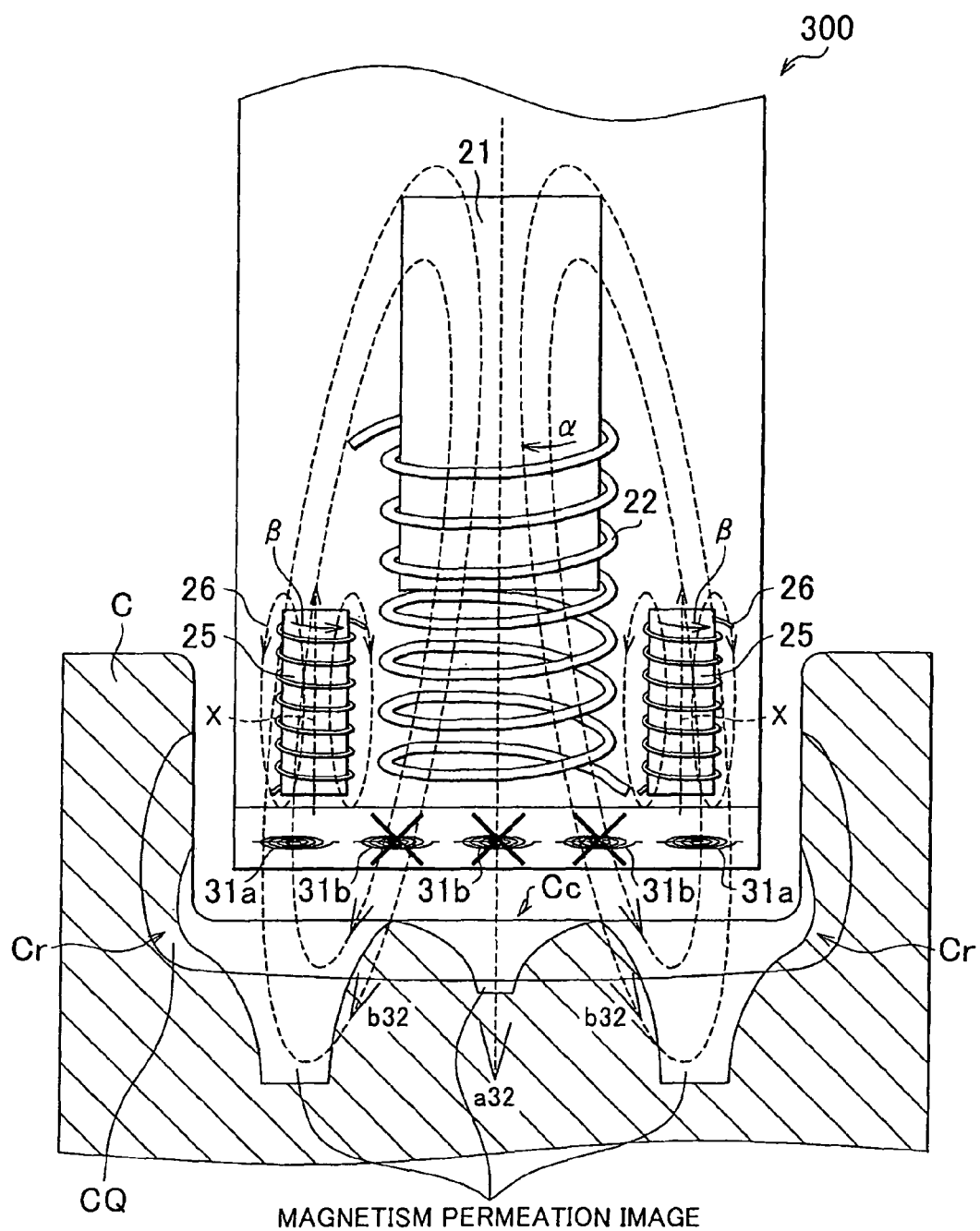
FIG. 17 is a schematic diagram of a second example of the eddy current measuring sensor according to the third embodiment.

Next, a second example applied to eddy current measurement performed while the magnetic field is intensified on the outside when measuring the hardening depth and the hardness of a hardened layer formed in steel using the eddy current measuring sensor 300 according to the third embodiment will now be described. In this example, an eddy current measurement such as that described above is performed while the main coil 22, the sub-cores 25, and the sub-coils 26 are moved to the tip end side of the eddy current measuring sensor 300, and the main core 21 is moved slightly to the base end side of the eddy current measuring sensor 300 with respect to the main coil 22, as shown in FIG. 17. In this example, a journal portion of a crankshaft C is used as the object of eddy wave measuring, and a hardened layer CQ is formed over a center portion Cc and an R portion Cr at both ends of the journal portion. Incidentally, this example may also be applied to a camshaft or a pin portion of the crankshaft C and the like.

In this example, the instant that current flows as shown by arrow α in FIG. 17 through the main coil 22, a downward magnetic field (arrow a32 in FIG. 17) is generated inside the main coil 22 according to the right-hand screw rule, and further, a rotating magnetic field (arrow b32 in FIG. 17) that circulates around the main coil 22, i.e., that flows alternately inside and outside the main coil 22, is generated. In addition, upward magnetic fields (arrows x in FIG. 17) are generated inside the sub-coils 26.

At this time, the upward magnetic field outside of the main coil 22 is attracted by the sub-coils 26, and at the same time, is also attracted to the main core 21 that has moved to the upper side. Therefore, a rotating magnetic field is generated in a shape similar to that of a tube having a diameter that gradually increases from the upper side to the lower side, as shown in FIG. 17, and the rotating magnetic field that forms the increased diameter portion acts on the crankshaft C. Forming the rotating magnetic field generated at the main coil 22 in a shape similar to that of a tube having a larger diameter at the portion of the crankshaft C in this way intensifies the magnetic field at the crankshaft C at the outside, and thus enables the eddy current generated by the rotating magnetic field acting on the crankshaft C to be stronger at the outside. In this way, in this example, performing an eddy current measurement as described above enables the eddy current to be measured while the magnetic field is intensified at the outside at the crankshaft C by the main core 21 and the sub-cores 25, as shown in the magnetism permeation image of FIG. 17.

The magnetic field in the vertical direction and the rotating magnetic field generated at the main coil 22 in this way acts strongly on the portion of the hardened layer CQ formed in the crankshaft C that is opposite the sub-coils 26 and generates an eddy current there, as shown in FIG. 17. At this time, an electromagnetic induction phenomenon causes the eddy current generated in the crankshaft C to take on a property in which it widens significantly near the surface of the object being measured. Also, the magnetic permeability of the unhardened portion is greater than the magnetic permeability of the hardened layer CQ, as shown in FIG. 1, so the magnetic field tends to be attracted to the unhardened portion. Therefore, the eddy current tends to expand at the R portions Cr where the boundary portion between the hardened layer CQ and the unhardened portion is. That is, as shown in FIG. 17, the eddy current can be expanded at the portions of the R portions Cr at both ends of the journal portion. In this example, the detection coils arranged opposite the portion where the eddy current is generated are the acknowledged detection coils 31*a*, and the detection coils positioned at the inner peripheral portion are the ignored detection coils 31*b*. The hardening depth and the hardness of the R portions Cr of the hardened layer CQ are measured by the acknowledged detection coils 31*a* based on only the signals that have detected the eddy current generated in the R portions Cr.

In this way, in this embodiment, by performing an eddy current measurement as described above, the detection region can be selected freely by selectively making the detection signals of the detection coils so as to be acknowledged or ignored as appropriate for the spread and the direction of the magnetic field. More specifically, it is possible to measure the hardening depth and the hardness of the journal portion or the pin portions of the crankshaft C only at the R portions Cr of both ends of the hardened layer CQ. Also, the measuring accuracy can be improved by measuring the eddy current while controlling the spread and direction of the magnetic field according to the hardening pattern. Further, the eddy current measurement can be performed accurately by using the eddy current measuring probe sensor 300, even with a component in which the outer diameter changes significantly, such as with the crankshaft C or a camshaft.

Figure 18:
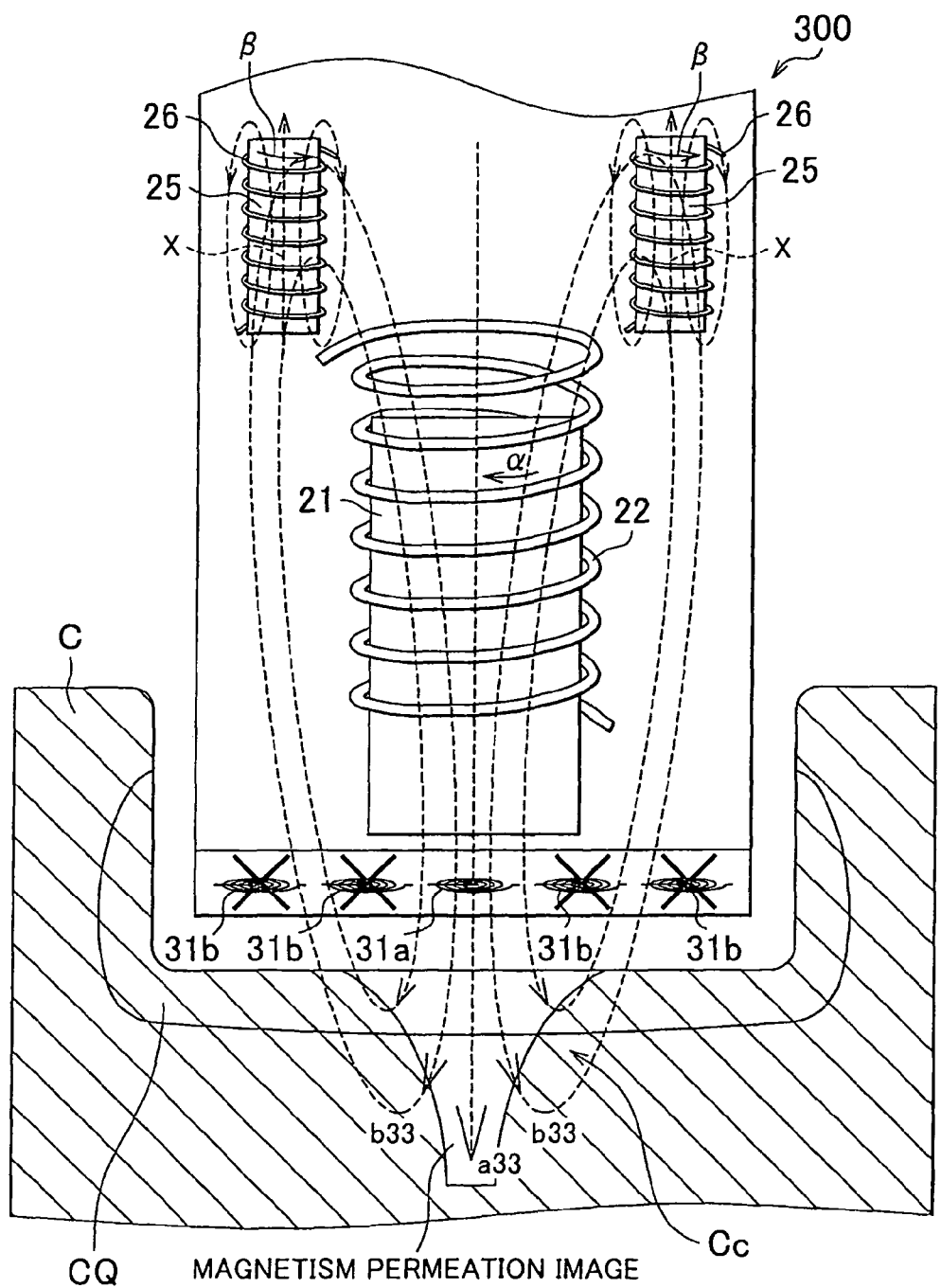
FIG. 18 is a schematic diagram of a third example of the eddy current measuring sensor according to the third embodiment.

Next, a third example applied to eddy current measurement performed while the magnetic field is intensified at the inside center portion when measuring the hardening depth and the hardness of a hardened layer formed in steel using the eddy current measuring sensor 300 according to the third embodiment will now be described. In this example, an eddy current measurement such as that described above is performed while the main core 21 is moved to the tip end side of the eddy current measuring sensor 300, the sub-cores 25 and the sub-coils 26 are moved to the base end side of the eddy current measuring sensor 300, and the main coil 22 is moved to an intermediate position with respect to the main core 21 and the sub-cores 25, as shown in FIG. 18. In this example as well, the journal portion of the crankshaft C is used as the object of eddy current measuring, and the hardened layer CQ is formed over a center portion Cc and an R portions at both ends of the journal portion.

In this example, the instant that current flows as shown by arrow α in FIG. 18 through the main coil 22, a downward magnetic field (arrow a33 in FIG. 18) is generated inside the main coil 22 according to the right-hand screw rule, and further, a rotating magnetic field (arrow b33 in FIG. 18) that circulates around the main coil 22, i.e., that flows alternately inside and outside the main coil 22, is generated. In addition, upward magnetic fields (arrows x in FIG. 18) are generated inside the sub-coils 26.

At this time, the upward magnetic field outside the main coil 22 is attracted to the sub-cores 25, and at the same time, the downward magnetic field inside the main coil 22 is attracted to the main core 21. Therefore, a rotating magnetic field is generated in a shape similar to that of a tube having a diameter that gradually decreases from the upper side to the lower side, as shown in FIG. 18, and the rotating magnetic field that forms the decreased diameter portion acts on the crankshaft C. Forming the rotating magnetic field generated at the main coil 22 in a shape similar to that of a tube having a smaller diameter at the portion of the crankshaft C in this way intensifies the magnetic field at the crankshaft C at the inside center portion, and thus enables the eddy current generated by the rotating magnetic field acting on the crankshaft C to be stronger at the inside center portion. In this way, in this example, performing an eddy current measurement as described above enables the eddy current to be measured while the magnetic field is intensified at the inside center portion of the crankshaft C by the main core 21 and the sub-cores 25, as shown in the magnetism permeation image of FIG. 18.

The magnetic field in the vertical direction and the rotating magnetic field generated at the main coil 22 in this way act strongly on the portion of a hardened layer CQ formed in the crankshaft C that is opposite the inside center portion of the eddy current measuring sensor 300 and generates an eddy current there, as shown in FIG. 18. That is, the eddy current acts on a portion of the center portion Cc of the journal portion, as shown in FIG. 18. In this example, the detection coil arranged opposite the portion where the eddy current is generated is the acknowledged detection coil 31a and the detection coils positioned at the other portions are the ignored detection coils 31b. The hardening depth and the hardness of the center portion Cc of the hardened layer CQ are measured by the acknowledged detection coils 31a based on only the signals that have detected the eddy current generated in the center portion Cc.

In this way, in this embodiment, by performing an eddy current measurement as described above, the detection region can be selected freely by selectively making the detection signals of the detection coils so as to be acknowledged or ignored as appropriate for the spread and the direction of the magnetic field. More specifically, it is possible to measure the hardening depth and the hardness of the journal portion or the pin portions of the crankshaft C only at the center portion Cc of the hardened layer CQ. Also, the measuring accuracy can be improved by measuring the eddy current while controlling the spread and direction of the magnetic field according to the hardening pattern.

Figure 19A:
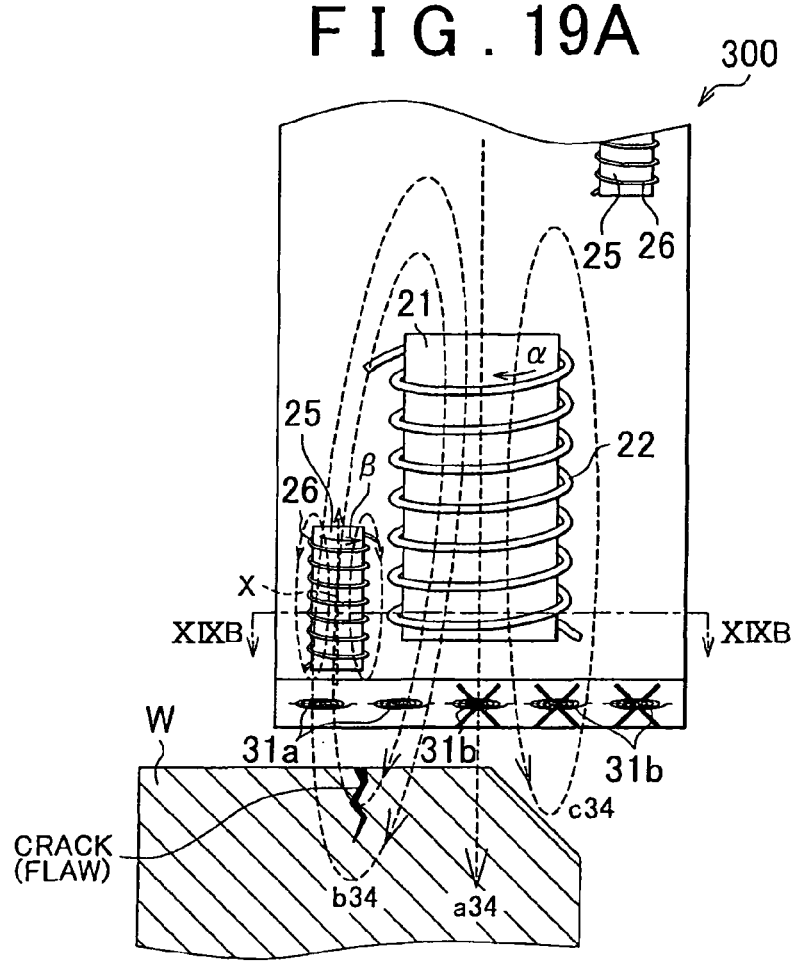
FIG. 19A is a schematic diagram of a fourth example of the eddy current measuring sensor according to the third embodiment.

Next, a fourth example applied to eddy current measurement performed while the magnetic field is intensified on one side when performing an eddy current using the eddy current measuring sensor 300 according to the third embodiment will now be described. In this example, an eddy current measurement such as that described above is performed while the main core 21 and the main coil 22 are moved to the tip end side of the eddy current measuring sensor 300, the sub-cores 25 and the sub-coils 26 on one side (i.e., the sub-cores 25 and the sub-coils 26 on the left side in FIGS. 19A and 19B) are moved to the tip end side of the eddy current measuring sensor 300, and the other sub-cores 25 and the other sub-coils 26 are moved to the base end side of the eddy current measuring sensor 300, such that the other sub-cores 25 and the other sub-coils 26 are separated from the main core 21 and the main coil 22, as shown in FIG. 19A. At this time, voltage is not applied to the sub-coils 26 that have been moved to the base end side.

In this example, the instant that current flows as shown by arrow α and arrow β in FIG. 19A through the main coil 22 and the sub-coils 26, a downward magnetic field (arrow a34 in FIG. 19A) is generated inside the main coil 22 according to the right-hand screw rule, and further, an upward magnetic field is generated outside the main coil 22. More specifically, a rotating magnetic field (arrow b34 and arrow c34 in FIG. 19A) that circulates around the main coil 22, i.e., that flows alternately inside and outside the main coil 22, is generated. In addition, an upward magnetic field (arrow x in FIG. 19A) is generated inside the sub-coils 26 on the left side.

Figure 19B:
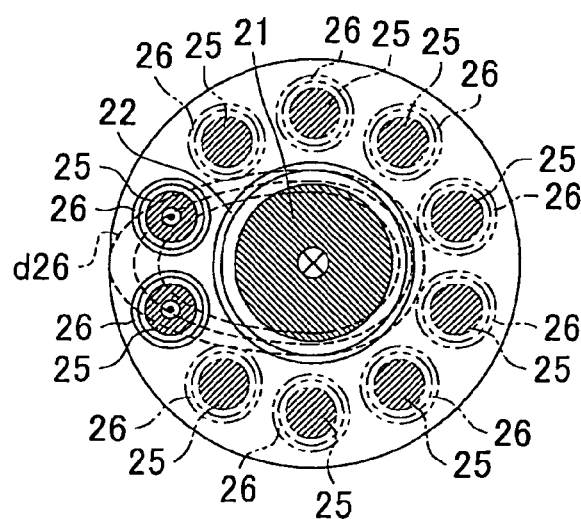
FIG. 19B is a sectional view taken along line XIXB-XIXB in FIG. 19A.

At this time, the upward magnetic field on the right side outside the main coil 22 is not affected by the sub-cores 25 on the upper right side, so a normal magnetic field is generated. On the other hand, the upward magnetic field on the left side outside the main coil 22 duplicates the direction of the upward magnetic fields generated by the sub-coils 26, so the upward magnetic field on the left side outside the main coil 22 is intensified, and at the same time, is attracted by the sub-coils 26. Therefore, a rotating magnetic field on the left side outside the main coil 22 is generated in a shape that is progressively offset to the left side from the upper side toward the lower side as shown in FIG. 19A, and the rotating magnetic field of the portion offset to the left acts strongly on the work W as shown in FIG. 19B. Having the shape of the strong rotating magnetic field generated at the main coil 22 be offset to the left at the portion of the work W further intensifies the magnetic field at the work W on one side, and thus enables the eddy current generated by the rotating magnetic field acting on the work W to be stronger on one side.

The magnetic field in the vertical direction and the rotating magnetic field generated at the main coil 22 in this way act on the portion of the work W that is opposite the left side of the eddy current measuring sensor 300 and generates an eddy current there, as shown in FIGS. 19A and 19B. In this example, the detection coils arranged opposite the portion where the eddy current is generated are the acknowledged detection coils 31a and the detection coils positioned at the other portions are the ignored detection coils 31b. The hardening depth and the hardness of a portion of the work W are measured by the acknowledged detection coils 31a based on only the signals that have detected the eddy current generated in the work W.

In this way, in this embodiment, by performing an eddy current measurement as described above, the detection region can be selected freely by selectively making the detection signals of the detection coils so as to be acknowledged or ignored as appropriate for the spread and direction of the magnetic field. More specifically, an eddy current can be generated in just a portion that has a crack (i.e., a flaw) even if the end portion of the work W is the object to be measured, as in FIG. 19A. By having the detection coils of that portion be the acknowledged detection coils 31a and making only those detection signals so as to be acknowledged while making the detection signals related to the detection of the eddy current at the edge portion so as to be ignored, it is possible to prevent the detection signal of the eddy current at the flawed portion from becoming buried in a detection signal related to the edge portion. In other words, the edge effect can be reduced in an eddy current measurement by a probe coil.

Next, an eddy current measuring sensor 400 according to a fourth embodiment of the invention will be described with reference to FIGS. 20A and 20B. Incidentally, to simplify the description, in FIG. 20A only the sub-cores 25 and the sub-coils 26 on the left and right ends are shown; all of the other sub-cores 25 and sub-coils 26 are omitted.

Figure 20A:
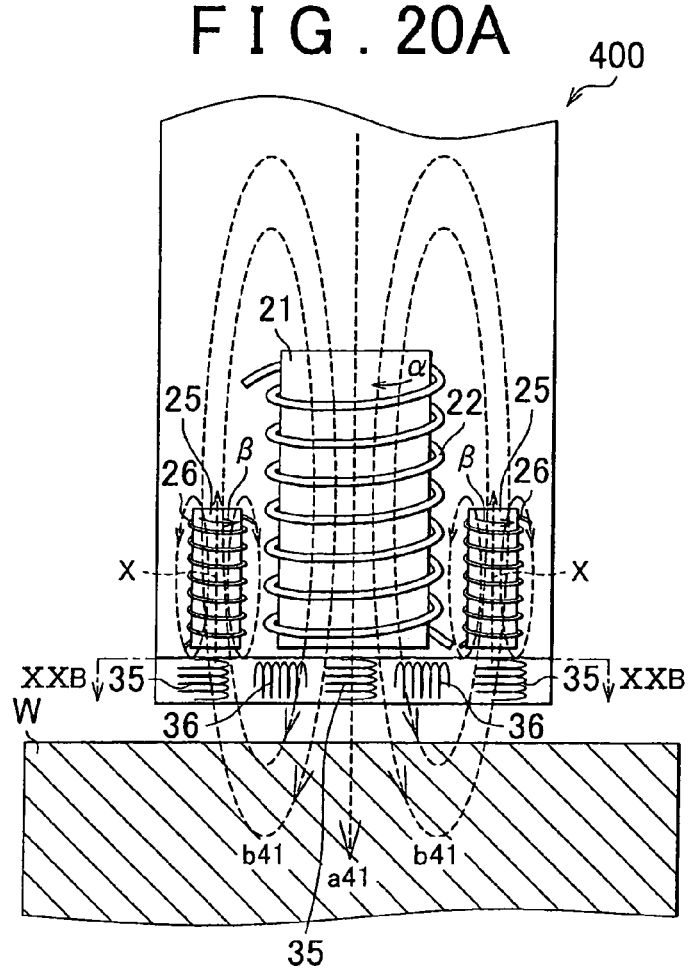
FIG. 20A is a schematic diagram of the structure of an eddy current measuring sensor according to a fourth embodiment of the invention.
Figure 20B:
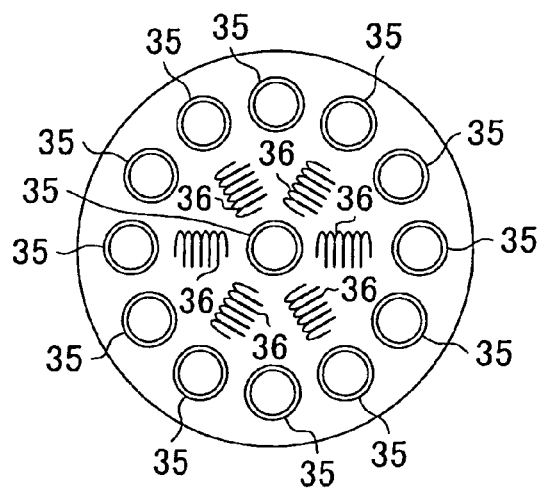
FIG. 20B is a sectional view taken along line XXB-XXB in FIG. 20A.

As shown in FIGS. 20A and 20B, the eddy current measuring probe sensor 400 according to this embodiment includes a plurality of vertical solenoid coils 35 and a plurality of horizontal solenoid coils 36 in a detecting portion. More specifically, the plurality of vertical solenoid coils 35 are arranged in positions in a tip end surface of an exciting portion that are opposite a main coil 22 and sub-coils 26 that together serve as a primary exciting portion, with the axial direction of each of the plurality of vertical solenoid coils 35 being the same as the axial direction of the main core 21. Similarly, the plurality of horizontal solenoid coils 36 are radially arranged, with their axes all pointing perpendicular to the axis of the main core 21, in positions in the tip end surface of the exciting portion that are between the main coil 22 and the sub-coils 26.

The vertical solenoid coils 35 according to this embodiment have relatively high detection sensitivity with respect to a magnetic field in the vertical (up-down) direction generated by the exciting portion as shown in FIG. 20A. That is, the vertical solenoid coils 35 have relatively high detection sensitivity with respect to a magnetic field in the direction of the central axis (i.e., a vertical magnetic field) in the eddy current measuring sensor 400 of this embodiment. On the other hand, the horizontal solenoid coils 36 have relatively high detection sensitivity with respect to a magnetic field in the horizontal direction (i.e., in the front-back and left-right directions) generated by the exciting portion. That is, the horizontal solenoid coils 36 have relatively high detection sensitivity with respect to a magnetic field in the direction perpendicular to the central axis (i.e., a horizontal magnetic field) in the eddy current measuring sensor 400 of this embodiment.

When performing an eddy current measurement using the eddy current measuring sensor 400 structured as described above, voltage is applied by an AC power supply to the main coil 22 and the sub-coils 26. The instant that current flows as shown by arrow α in FIG. 20A through the main coil 22, a downward magnetic field is generated inside the main coil 22 according to the right-hand screw rule (see arrow a41 in FIG. 20A). Also, the instant that current flows as shown by arrow β in FIG. 20A through the sub-coils 26, an upward magnetic field is generated inside the sub-coils 26 according to the right-hand screw rule (see arrow x in FIG. 20A).

The magnetic field generated as described above causes electromagnetic induction, which in turn generates an eddy current in the work W that is a magnetic body. Furthermore, with the generation of the eddy current at the surface of the work W, the magnetic flux penetrates the detecting portion that then measures the induced voltage that accompanies the generation of the eddy current at the surface of the work W. At this time, the vertical magnetic field can be detected with good sensitivity by the vertical solenoid coils 35, and the horizontal magnetic field can be detected with good sensitivity by the horizontal solenoid coils 36.

According to the eddy current measuring sensor 400 of this embodiment, by providing the detecting portion with the plurality of vertical solenoid coils 35 and the plurality of horizontal solenoid coils 36, the eddy current detection sensitivity by the detecting portion is able to be increased, and the detection efficiency is able to be improved.

Figure 21:
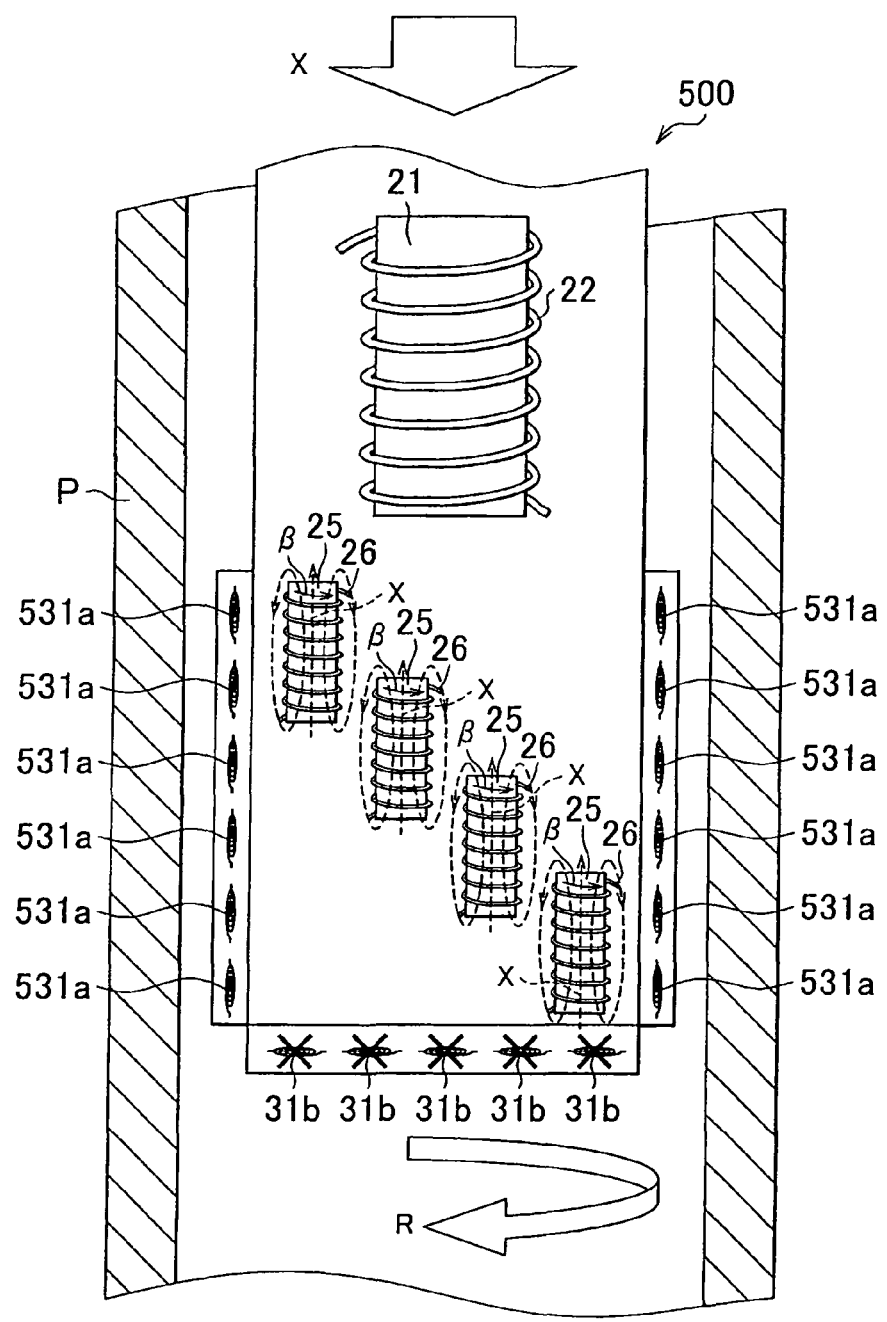
FIG. 21 is a schematic diagram of the structure of an eddy current measuring sensor according to a fifth embodiment of the invention.

Next, an eddy current measuring sensor 500 according to a fifth embodiment of the invention will be described with reference to FIG. 21. As shown in FIG. 21, the eddy current measuring probe sensor 500 according to this embodiment is provided with a plurality of detection coils 531a as detecting portions that are arranged adjacent to, and to the outside of, sub-cores 25 and sub-coils 26 that serve as a secondary exciting portion, in the radial direction of the main core 21. More specifically, the plurality of detection coils 531a are arranged at fixed intervals in the axial direction of the eddy current measuring sensor 500, to the outside of the sub-cores 25 and the sub-coils 26.

Structuring the eddy current measuring sensor 500 of this embodiment as described above enables the eddy current measuring sensor 500 to be used as an inner eddy current measuring sensor that takes an eddy current measurement of the inner surface portion of a hole or a tubular work or the like over a wide area at one time. When performing an eddy current measurement with the eddy current measuring sensor 500 of this embodiment, the main core 21 and the main coil 22 are moved to the base end side of the eddy current measuring sensor 500 away from the sub-cores 25 and the sub-coils 26, as shown in FIG. 21. Also, the sub-cores 25 and the sub-coils 26 are arranged in a spiral on the tip end side of the eddy current measuring sensor 500. Furthermore, the eddy current measuring sensor 500 is inserted into a pipe P and the eddy current measurement is performed moving the eddy current measuring sensor 500 in direction of arrow X while rotating it about its axis shown by arrow R in FIG. 21. Incidentally, the sub-cores 25 and the sub-coils 26 may also be arranged on the same plane that is perpendicular to the axis of the eddy current measuring sensor 500, instead of being arranged in a spiral, or they may be arranged in a spiral in order to reduce the affect that the generated magnetic fields have on each other.

When an eddy current measurement of the inner surface portion of the pipe P is made using the eddy current measuring sensor 500 structured as described above, voltage is applied by the AC power supply only to the sub-coils 26. The instant that current flows as shown by arrow β in FIG. 21 through the sub-coils 26, an upward magnetic field is generated inside the sub-coils 26 according to the right-hand screw rule (see arrow x in FIG. 21).

The magnetic field generated as described above causes electromagnetic induction, which in turn generates an eddy current in the pipe P that is a magnetic body. Furthermore, with the generation of the eddy current at the surface of the pipe P, the magnetic flux penetrates the detection coils 531a that then measure the induced voltage that accompanies the generation of the eddy current at the surface of the pipe P. Incidentally, at this time, all of the detection signals from the ignored detection coils 31b at the tip end are acknowledged.

As described above, the eddy current measuring sensor 500 can be used as an inner eddy current measuring sensor that performs an eddy current measurement of the inner surface portion of a hole or a tubular work or the like over a wide area at one time by arranging the plurality of detection coils 531a at fixed widths in the axial direction of the eddy current measuring sensor 500 to the outside of the sub-cores 25 and the sub-coils 26. In other words, the eddy current measuring sensor 500 can also be used as an inner eddy current measuring sensor as well as a surface eddy current measuring sensor as in the embodiments described above.

While some embodiments of the invention have been illustrated above, it is to be understood that the invention is not limited to details of the illustrated embodiments, but may be embodied with various changes, modifications Or improvements, which may occur to those skilled in the art, without departing from the scope of the invention.

The invention claimed is:
1. An eddy current measuring probe sensor comprising:
an exciting portion that i) includes a primary exciting portion that includes a main core formed of a cylindrical magnetic body and a main coil that is a solenoid coil wound in a circumferential direction around the main core, and a plurality of secondary exciting portions that include sub-cores formed of cylindrical magnetic bodies that are arranged around the primary exciting portion in a manner such that an axial direction of each sub-core is the same as an axial direction of the main core, the plurality of secondary exciting portions being configured to change the position of each sub-core independently in the axial direction of the main core relative to the primary exciting portion, and ii) applies a predetermined alternating current excitation signal to a component to be measured; and a detecting portion that detects a detection signal according to an eddy current from the component to be measured to which the predetermined alternating current excitation signal has been applied.

2. The sensor according to claim 1, wherein each of the secondary exciting portions includes a sub-coil that is a solenoid coil that is wound in a circumferential direction around the sub-core, and each of the secondary exciting portions is configured such that a direction of magnetic flux that is generated at the main coil of the primary exciting portion and penetrates the main core is opposite a direction of magnetic flux that is generated in the sub-coil of each of the secondary exciting portions and penetrates the sub core.

3. The sensor according to claim 1, wherein the primary exciting portion is configured to change the relative positions of the main coil and the main core independently in the axial direction of the main core.

4. The sensor according to claim 1, wherein the detecting portion includes a plurality of detection coils radially arranged centered around an axial portion of the primary exciting portion; and the plurality of detection coils are each independently and selectively made so as to be acknowledged or ignored with regards to detecting the detection signal.

5. The sensor according to claim 1, wherein the detecting portion includes a plurality of pancake coils or a plurality of planar coils, that are arranged over an entire tip end surface of the exciting portion, and the tip end surface is a surface on the side of the component to be measured.

6. The sensor according to claim 1, wherein the detecting portion includes a plurality of vertical solenoid coils arranged in positions in a tip end surface of the exciting portion that are opposite the primary exciting portion and the secondary exciting portion, in a manner such that an axial direction of each of the plurality of vertical solenoid coils is the same as the axial direction of the main core, and a plurality of horizontal solenoid coils radially arranged in positions in the tip end surface of the exciting portion that are between the primary exciting portion and the secondary exciting portion, in a manner such that the axial direction of each of the plurality of horizontal solenoid coils is perpendicular to the axis of the main core.

7. The sensor according to claim 1, wherein the detecting portion includes a plurality of detection coils that are arranged adjacent to the secondary exciting portions and to the outside of the secondary exciting portions in a radial direction of the main core.

8. The sensor according to claim 1, wherein the predetermined alternating current excitation signal is a magnetic field that is generated by applying a predetermined alternating current voltage to the main coil.

9. The sensor according claim 1, wherein the detection signal is voltage induced by the eddy current.

10. An inspection method characterized by comprising:
inspecting a component to be measured by performing an eddy current measurement using an eddy current measuring probe sensor comprising: an exciting portion that i) includes a primary exciting portion that includes a main core formed of a cylindrical magnetic body and a main coil that is a solenoid coil wound in a circumferential direction around the main core, and a plurality of secondary exciting portions that include sub-cores formed of cylindrical magnetic bodies that are arranged around the primary exciting portion in a manner such that an axial direction of each sub-core is the same as an axial direction of the main core, the plurality of secondary exciting portions being configured to change the position of each sub-core independently in the axial direction of the main core relative to the primary exciting portion, and ii) applies a predetermined alternating current excitation signal to the component to be measured; and a detecting portion that detects a detection signal according to an eddy current from the component to be measured to which the predetermined alternating current excitation signal has been applied.

* * * * *